US010736752B1

(12) United States Patent
Schifano et al.

(10) Patent No.: US 10,736,752 B1
(45) Date of Patent: Aug. 11, 2020

(54) MULTI-MATERIAL MULTI-COMPONENT SPINAL IMPLANT

(71) Applicant: Omnia Medical, LLC, Morgantown, WV (US)

(72) Inventors: Troy Schifano, Morgantown, WV (US); Daniel Johnson, Westlake, OH (US); Stephen Anderson, Folsom, CA (US); Peter Materna, Metuchen, NJ (US)

(73) Assignee: Omnia Medical, LLC, Morgantown, WV (US)

( * ) Notice: Subject to any disclaimer, the term of this patent is extended or adjusted under 35 U.S.C. 154(b) by 0 days.

(21) Appl. No.: 16/169,387

(22) Filed: Oct. 24, 2018

Related U.S. Application Data

(60) Provisional application No. 62/576,203, filed on Oct. 24, 2017.

(51) Int. Cl.
| | |
|---|---|
| *A61F 2/44* | (2006.01) |
| *A61F 2/30* | (2006.01) |
| *A61F 2/28* | (2006.01) |

(52) U.S. Cl.
CPC ........ *A61F 2/4425* (2013.01); *A61F 2/30771* (2013.01); *A61F 2/4455* (2013.01); *A61F 2002/2835* (2013.01); *A61F 2310/00023* (2013.01); *A61F 2310/00293* (2013.01)

(58) Field of Classification Search
CPC ...... A61F 2/4455; A61F 2/447; A61F 2/4465; A61F 2/30771; A61F 2002/30006; A61F 2002/30013
See application file for complete search history.

(56) References Cited

U.S. PATENT DOCUMENTS

| | | |
|---|---|---|
| 5,397,364 A | 3/1995 | Kozak et al. |
| 6,102,948 A | 8/2000 | Brosnahan, III |
| 6,520,993 B2 | 2/2003 | James et al. |
| 6,558,424 B2 | 5/2003 | Thalgott |
| 6,569,201 B2 | 5/2003 | Moumene et al. |
| 6,726,720 B2 | 4/2004 | Ross et al. |

(Continued)

FOREIGN PATENT DOCUMENTS

WO    WO 2005063151    7/2005

*Primary Examiner* — Julianna N Harvey
(74) *Attorney, Agent, or Firm* — Peter Materna

(57) ABSTRACT

An implantable medical device, such as an intervertebral spacer, may comprise a polymeric component and a metallic component. The metallic component can contain both porous metal and substantially-solid metal. The polymeric material can contain particles of an osseointegrative material. The metallic component can be more protruding toward bone than the polymeric component while having a smaller dimension of roughness than the polymeric component. In embodiments, the pin may press-fit against substantially solid metal. The porous metal may surround solid metal which in turn may surround the pin. The pin may have a press-fit with metal and a looser fit with polymeric component, if the metal components and polymeric components are trapped. A pin may connect superior and inferior metal components by a press-fit. The central opening may be exposed to porous metal and also to substantially-solid metal and to polymer. Specific geometries of implants are disclosed.

13 Claims, 29 Drawing Sheets

(56) References Cited

U.S. PATENT DOCUMENTS

| | | |
|---|---|---|
| 7,018,416 B2 | 3/2006 | Hanson et al. |
| 7,037,339 B2 | 5/2006 | Houfburg |
| 7,303,583 B1 | 12/2007 | Schar et al. |
| 7,621,960 B2 | 11/2009 | Boyd et al. |
| 7,662,186 B2 | 2/2010 | Bagga et al. |
| 7,776,093 B2 | 8/2010 | Wolek et al. |
| 7,799,083 B2 | 9/2010 | Smith et al. |
| 7,875,075 B2 | 1/2011 | Schwab |
| 7,918,891 B1 | 4/2011 | Curran et al. |
| 7,947,044 B2 | 5/2011 | Ullrich, Jr. et al. |
| 7,998,212 B2 | 8/2011 | Schwab et al. |
| 8,097,036 B2 | 1/2012 | Cordaro et al. |
| 8,187,334 B2 | 5/2012 | Curran et al. |
| 8,241,359 B2 | 8/2012 | Davis et al. |
| 8,246,686 B1 | 8/2012 | Curran et al. |
| 8,262,737 B2 | 9/2012 | Bagga et al. |
| 8,273,127 B2 | 9/2012 | Jones et al. |
| 8,277,508 B2 | 10/2012 | Trieu |
| 8,353,962 B2 | 1/2013 | Eckman |
| 8,361,150 B2 | 1/2013 | Zhang et al. |
| 8,361,156 B2 | 1/2013 | Curran et al. |
| 8,383,024 B2 | 2/2013 | Morrissette et al. |
| 8,403,991 B2 | 3/2013 | Ullrich, Jr. et al. |
| 8,414,650 B2 | 4/2013 | Bertele et al. |
| 8,435,242 B2 | 5/2013 | Ullrich, Jr. et al. |
| 8,435,302 B2 | 5/2013 | Ullrich, Jr. et al. |
| 8,480,749 B2 | 7/2013 | Ullrich, Jr. et al. |
| 8,496,710 B2 | 7/2013 | Bagga et al. |
| 8,545,568 B2 | 10/2013 | Ullrich, Jr. et al. |
| 8,551,176 B2 | 10/2013 | Ullrich, Jr. et al. |
| 8,562,684 B2 | 10/2013 | Ullrich, Jr. et al. |
| 8,562,685 B2 | 10/2013 | Ullrich, Jr. et al. |
| 8,563,024 B2 | 10/2013 | Bratt et al. |
| 8,574,301 B2 | 11/2013 | Curran et al. |
| 8,585,765 B2 | 11/2013 | Ullrich, Jr. et al. |
| 8,585,766 B2 | 11/2013 | Ullrich, Jr. et al. |
| 8,585,767 B2 | 11/2013 | Ullrich, Jr. et al. |
| 8,591,590 B2 | 11/2013 | Ullrich, Jr. et al. |
| 8,608,804 B2 | 12/2013 | Curran et al. |
| 8,617,248 B2 | 12/2013 | Ullrich, Jr. et al. |
| 8,652,373 B2 | 2/2014 | Kar et al. |
| 8,685,105 B2 | 4/2014 | Curran et al. |
| 8,709,083 B2 | 4/2014 | Duffield et al. |
| 8,728,166 B2 | 5/2014 | Schwab |
| 8,729,150 B2 | 5/2014 | Jarman-Smith et al. |
| 8,753,396 B1 | 6/2014 | Hockett et al. |
| 8,758,442 B2 | 6/2014 | Ullrich, Jr. et al. |
| 8,758,443 B2 | 6/2014 | Ullrich, Jr. et al. |
| 8,764,832 B2 | 7/2014 | Schwab et al. |
| 8,795,373 B2 | 8/2014 | Jones et al. |
| 8,814,939 B2 | 8/2014 | Ullrich, Jr. et al. |
| 8,814,940 B2 | 8/2014 | Curran et al. |
| 8,821,912 B2 | 9/2014 | Crudden et al. |
| 8,829,096 B2 | 9/2014 | Jarman-Smith |
| 8,834,571 B2 | 9/2014 | Bagga et al. |
| 8,840,914 B2 | 9/2014 | Crudden et al. |
| 8,900,309 B2 | 12/2014 | James et al. |
| 8,940,053 B2 | 1/2015 | Ullrich, Jr. et al. |
| 8,961,606 B2 | 2/2015 | Laskowitz et al. |
| 8,992,619 B2 | 3/2015 | Patterson et al. |
| 8,992,622 B2 | 3/2015 | Ullrich, Jr. et al. |
| 9,011,546 B2 | 4/2015 | Ullrich, Jr. et al. |
| 9,089,428 B2 | 4/2015 | Bertele et al. |
| 9,107,765 B2 | 8/2015 | Ghiselli et al. |
| 9,114,023 B2 | 8/2015 | Kana et al. |
| 9,125,756 B2 | 9/2015 | Ullrich, Jr. et al. |
| 9,132,576 B2 | 9/2015 | Crudden et al. |
| 9,180,021 B2 | 11/2015 | Curran et al. |
| 9,238,319 B2 | 1/2016 | Gfeller et al. |
| 9,295,561 B2 | 3/2016 | Ball et al. |
| 9,314,337 B2 | 4/2016 | Patterson et al. |
| 9,327,051 B2 | 5/2016 | Ullrich, Jr. et al. |
| 9,364,342 B2 | 6/2016 | Walkenhorst et al. |
| 9,370,435 B2 | 6/2016 | Walkenhorst et al. |
| 9,375,321 B2 | 6/2016 | Whang et al. |
| 9,398,960 B2 | 7/2016 | Rosen et al. |
| 9,414,935 B2 | 8/2016 | McDonough et al. |
| 9,427,325 B2 | 8/2016 | Stinchfield et al. |
| 9,427,329 B2 | 8/2016 | James et al. |
| 9,433,511 B2 | 9/2016 | Bagga et al. |
| 9,439,779 B2 | 9/2016 | Zhang et al. |
| 9,456,905 B2 | 10/2016 | Borden et al. |
| 9,474,627 B2 | 10/2016 | Curran et al. |
| 9,492,584 B2 | 11/2016 | Crudden et al. |
| 9,498,336 B2 | 11/2016 | Doran et al. |
| 9,498,349 B2 | 11/2016 | Patterson et al. |
| 9,504,584 B1 | 11/2016 | Stein et al. |
| 9,517,142 B2 | 12/2016 | Pinto et al. |
| 9,539,102 B2 | 1/2017 | Klimek |
| 9,636,234 B2 | 5/2017 | Gfeller et al. |
| 9,655,745 B2 | 5/2017 | Patterson et al. |
| 9,693,874 B2 | 7/2017 | Fang et al. |
| 9,700,431 B2 | 7/2017 | Nebosky et al. |
| 9,713,535 B2 | 7/2017 | Davis et al. |
| 9,744,053 B2 | 8/2017 | Curran et al. |
| 9,763,787 B2 | 9/2017 | Bianchi et al. |
| 9,788,972 B2 | 10/2017 | Flickinger et al. |
| 9,788,973 B2 | 10/2017 | Lynn et al. |
| 9,833,319 B2 | 12/2017 | Gerber et al. |
| 9,848,995 B2 | 12/2017 | Ullrich, Jr. et al. |
| 9,987,051 B2 | 6/2018 | Nunley et al. |
| 1,011,175 A1 | 10/2018 | Patterson et al. |
| 1,018,292 A1 | 1/2019 | Willis et al. |
| 2002/0106393 A1 | 8/2002 | Bianchi et al. |
| 2004/0115172 A1 | 6/2004 | Bianchi et al. |
| 2004/0127993 A1 | 7/2004 | Kast et al. |
| 2007/0260324 A1 | 11/2007 | Joshi et al. |
| 2008/0154378 A1 | 6/2008 | Pelo |
| 2008/0161927 A1 | 7/2008 | Savage et al. |
| 2008/0215098 A1 | 9/2008 | Imwinkelried et al. |
| 2009/0138096 A1 | 5/2009 | Myerson et al. |
| 2009/0276053 A1 | 11/2009 | Brown et al. |
| 2010/0076559 A1 | 3/2010 | Bagga et al. |
| 2010/0094426 A1 | 4/2010 | Grohowski, Jr. et al. |
| 2011/0012280 A1 | 1/2011 | Deslauriers et al. |
| 2011/0190888 A1* | 8/2011 | Bertele ............... A61F 2/30907 623/17.11 |
| 2011/0282454 A1 | 11/2011 | Ullrich, Jr. et al. |
| 2012/0191190 A1* | 7/2012 | Trieu .................... A61F 2/442 623/17.11 |
| 2012/0239153 A1* | 9/2012 | Ullrich, Jr. ............ A61F 2/4465 623/17.16 |
| 2012/0265306 A1 | 10/2012 | Trieu |
| 2013/0171443 A1 | 7/2013 | Morrissette et al. |
| 2014/0257492 A1 | 9/2014 | Schwab et al. |
| 2014/0277461 A1* | 9/2014 | Nebosky .................. A61F 2/44 623/17.11 |
| 2015/0012100 A1 | 1/2015 | Ullrich, Jr. et al. |
| 2015/0045890 A1 | 2/2015 | Lefebvre et al. |
| 2015/0112439 A1 | 4/2015 | Ullrich, Jr. et al. |
| 2015/0157465 A1 | 6/2015 | Kirschman |
| 2015/0351929 A1 | 12/2015 | Ullrich, Jr. et al. |
| 2015/0359639 A1 | 12/2015 | Ullrich, Jr. et al. |

\* cited by examiner

Cephalad-caudal direction

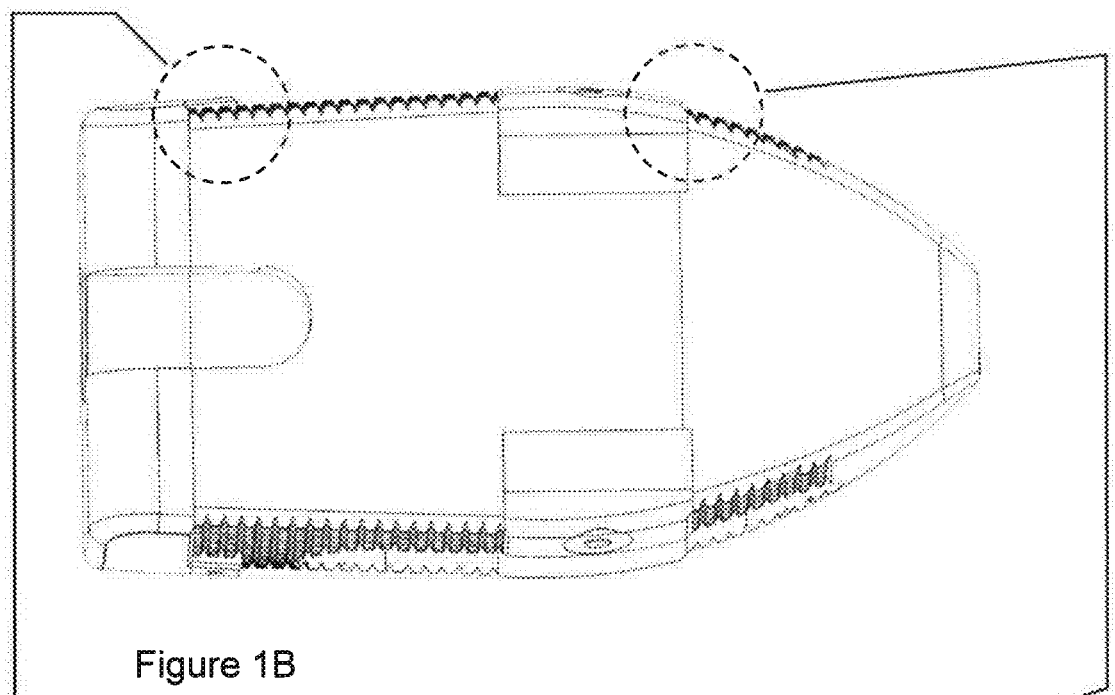
Figure 1B
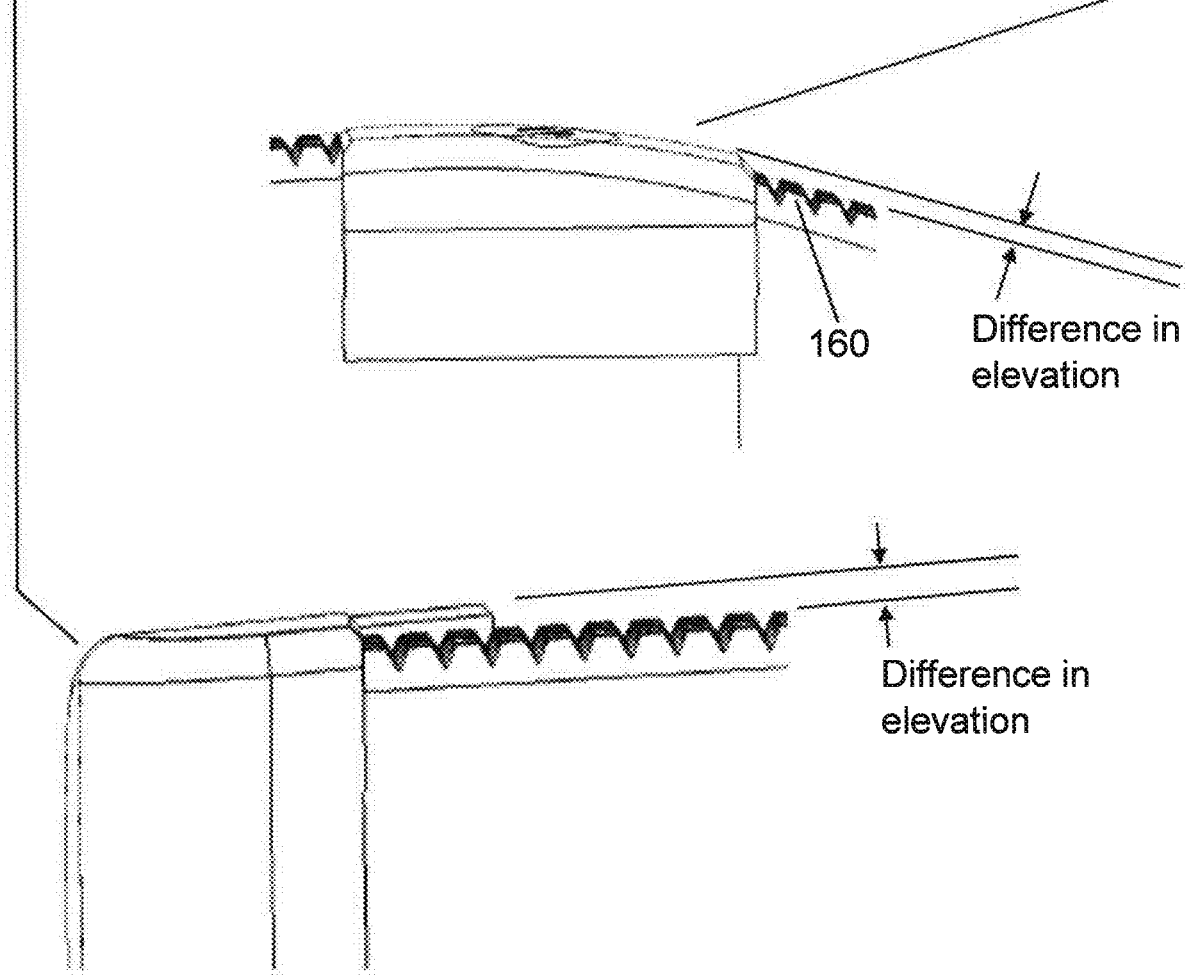

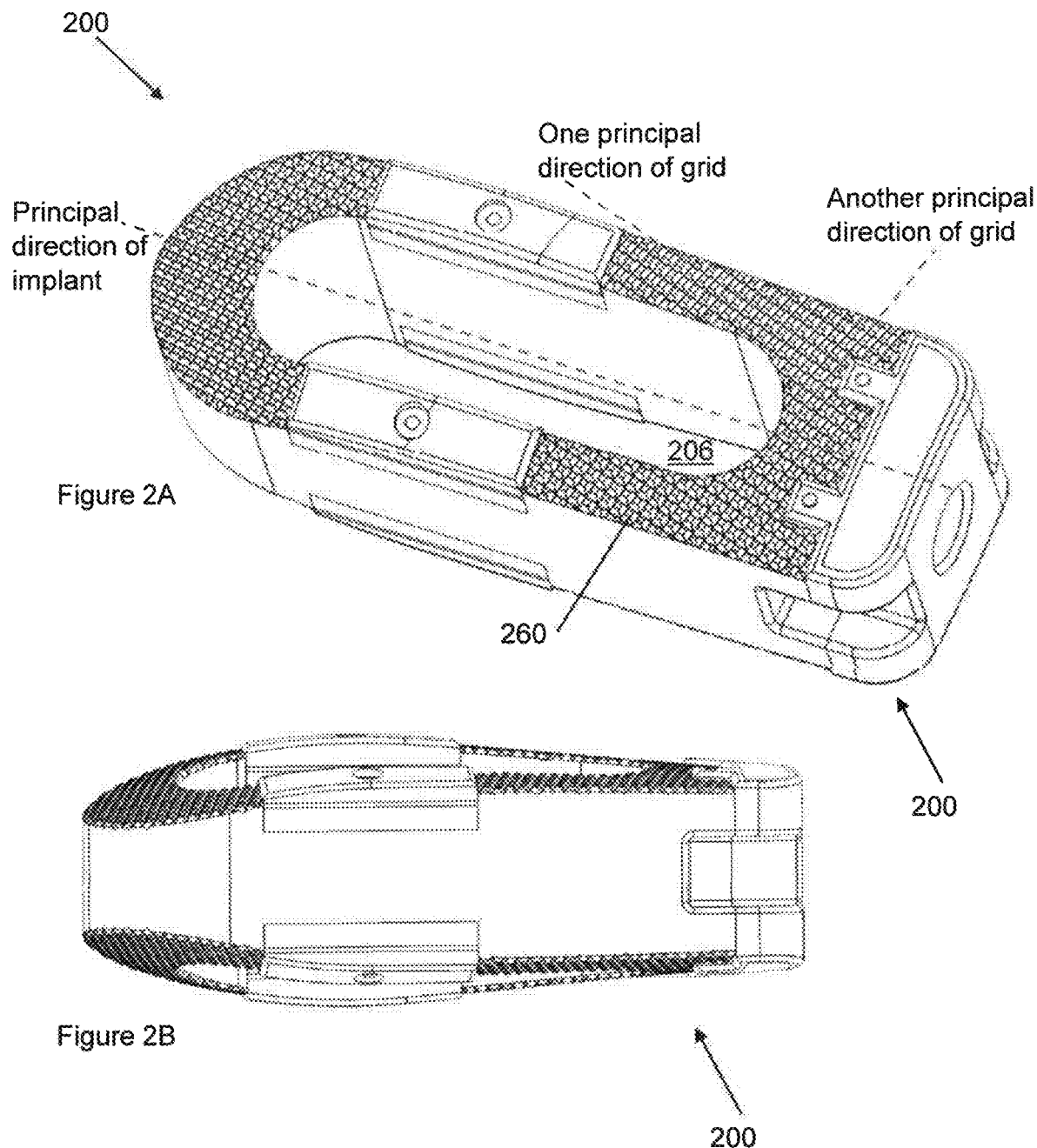

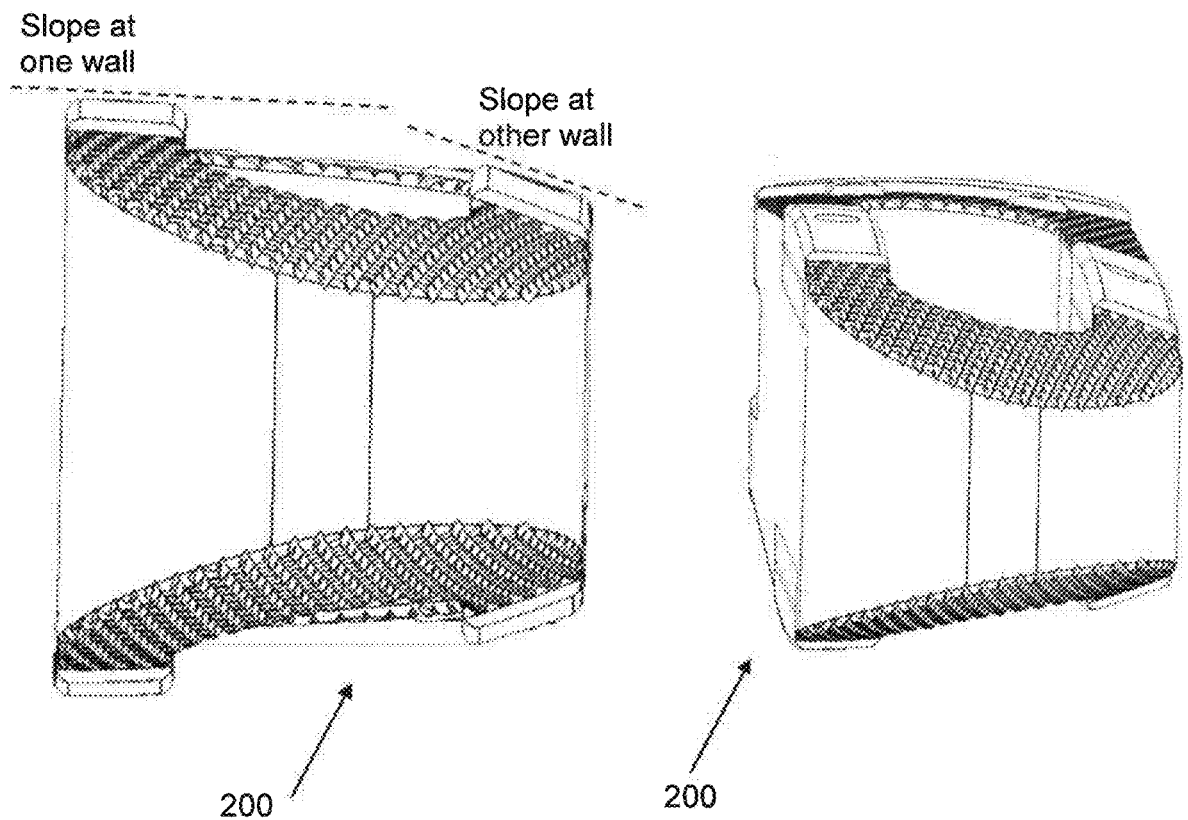
Figure 2C
Figure 2D
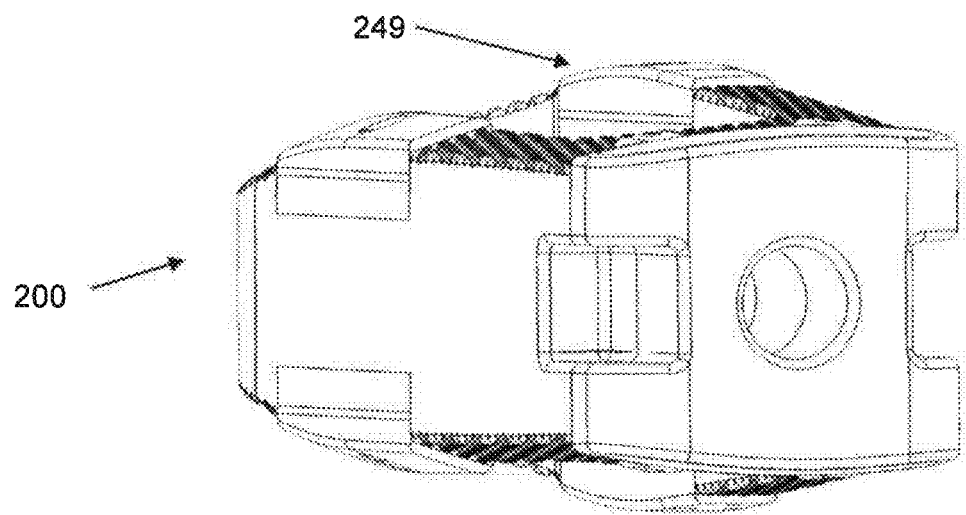
Figure 2E

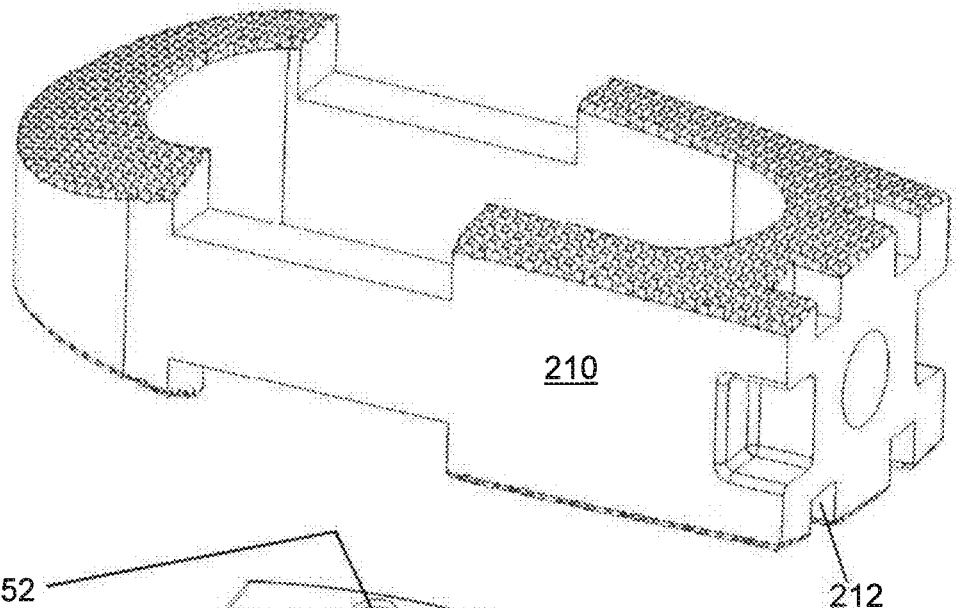
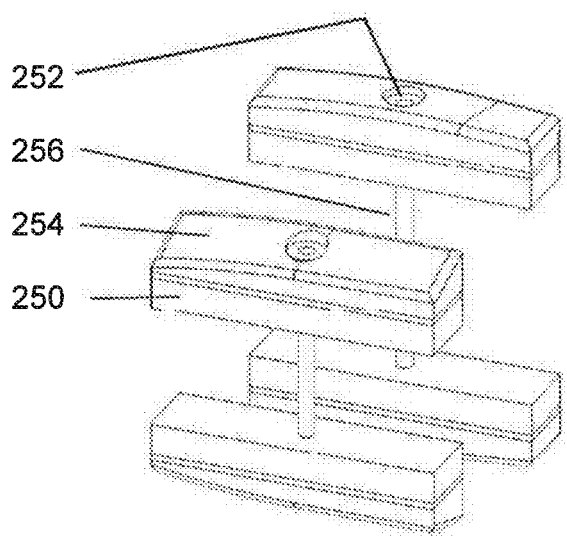
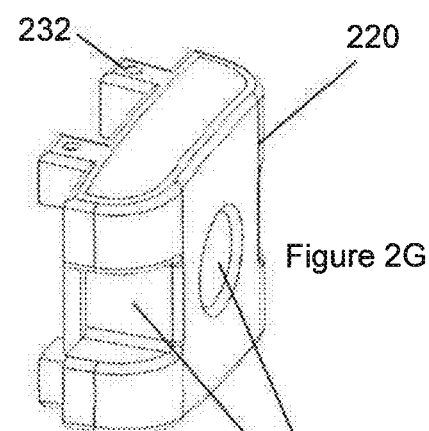
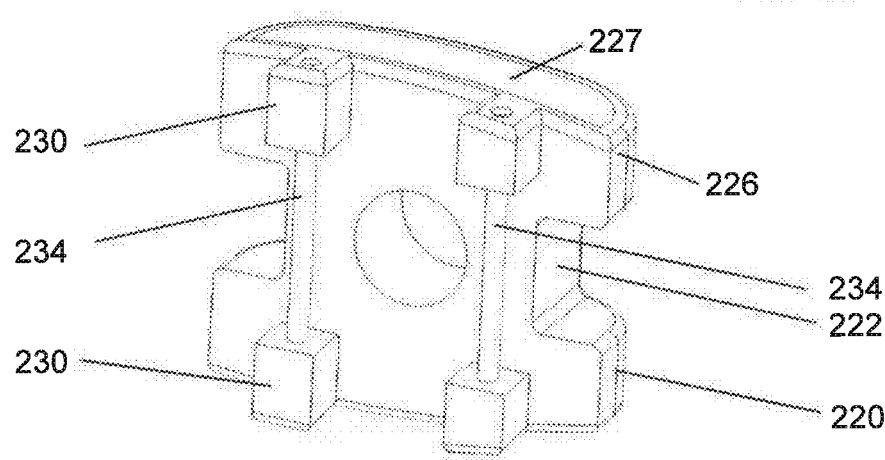
Figure 2F
Figure 2G
Figure 2H

US 10,736,752 B1

MULTI-MATERIAL MULTI-COMPONENT SPINAL IMPLANT

CROSS-REFERENCE TO RELATED APPLICATION

This patent application claims the benefit of U.S. Provisional patent application Ser. No. 62/576,203, filed Oct. 24, 2017, which is incorporated herein by reference in its entirety.

FIELD OF THE INVENTION

Embodiments of the invention pertain to spinal implants.

BACKGROUND OF THE INVENTION

Numerous designs of spinal implants exist. However, it is still desirable to optimize osseointegration and to improve certain design features.

SUMMARY OF THE INVENTION

In an embodiment of the invention, there may be provided an implantable device, the device comprising a polymeric component having a polymeric component bone-facing surface and a metallic component having a metallic component bone-facing surface, the polymeric component and the metallic component being mechanically joined to each other, the device having an external bone-facing surface that is partially the polymeric component bone-facing surface and partially the metallic component bone-facing surface adjacent to the polymeric component bone-facing surface, wherein the metallic component bone-facing surface is more protruding from the device in a bone-facing direction than is the polymeric component bone-facing surface, and wherein the polymeric component bone-facing surface has polymeric roughness features on a larger dimensional scale than metallic roughness features of the metallic component bone-facing surface.

In an embodiment of the invention, there may be provided an implantable device, the device having a first bone-facing surface and an opposed second bone-facing surface and having a central opening extending from the first bone-facing surface to the second bone-facing surface, the device comprising a polymeric component, the device comprising a metallic component, the metallic component and the polymeric component being mechanically connected to each other, wherein the metallic component comprises a substantially solid region and a porous region, the substantially solid region and the porous region being integrally adjoined to each other, wherein one of the bone-facing surfaces of the device comprises a surface of the polymeric component and a surface of the porous region of the metallic component and a surface of the substantially solid region of the metallic component.

In an embodiment of the invention, there may be provided an implantable device, the device having a first bone-facing surface and an opposed second bone-facing surface and having a central opening extending from the first bone-facing surface to the second bone-facing surface, the device comprising a polymeric component, the device comprising a metallic component, the metallic component and the polymeric component being mechanically connected to each other, wherein the metallic component comprises a substantially solid region and a porous region, the substantially solid region and the porous region being integrally adjoined to each other, the substantially solid region having a density at least 90% of a solid density of a metal of which the metallic component is made, the porous region having a density less than 80% of the metal of which the metallic component is made, wherein in the metallic component, the porous region is part of one of the bone-facing surfaces, and the porous region also faces the central opening.

In an embodiment of the invention, there may be provided an implantable device, the device having a first bone-facing surface and an opposed second bone-facing surface and having a central opening extending from the first bone-facing surface to the second bone-facing surface, the device comprising a polymeric component and a first metallic component on the first bone-facing surface and a second metallic component on the second bone-facing surface, further comprising a pin, wherein the pin occupies a hole in the first metallic component and occupies a hole in the second metallic component and occupies a hole through the polymeric component, wherein the pin is mechanically joined to the hole in the first metallic component and the pin is mechanically joined to the hole in the second metallic component.

In an embodiment of the invention, there may be provided an implantable device, the device having a first bone-facing surface and an opposed second bone-facing surface and having a central opening extending from the first bone-facing surface to the second bone-facing surface, the device comprising a polymeric component, the device comprising a metallic component that is mechanically connected to the polymeric component, wherein the metallic component comprises a substantially solid region and a porous region, wherein the porous region of the metallic component has a density less than 80% of a density of metal of which the metallic component is made, and the substantially solid region has a density more than 90% of a density of metal of which the metallic component is made, wherein the metallic component has a metallic component outwardly-facing surface that is part of one of the bone-facing surfaces, and the metallic component has a metallic component inwardly-facing surface opposed to the metallic component outwardly-facing surface, wherein the metallic component inwardly-facing surface has at least a majority of its surface being the substantially solid region, wherein the metallic component outwardly-facing surface contains both a surface of the porous region and a surface of the substantially solid region.

In an embodiment of the invention, there may be provided an implantable device, the device having a first bone-facing surface and an opposed second bone-facing surface and having a central opening extending from the first bone-facing surface to the second bone-facing surface, the device comprising a polymeric component, the device comprising a first metallic component that is mechanically connected to the polymeric component, further comprising a pin that passes through at least one hole in the polymeric component and at least one hole in the first metallic component, wherein the pin is a press-fit in one of the holes and is looser than a press-fit in another of the holes, wherein, in the absence of the pin, the polymeric component and the first metallic component have a relationship with each other that at least partially constrains relative motion between the polymeric component and the metallic component, wherein when the pin is installed, the polymeric component and the metallic component are further constrained with respect to each other.

In an embodiment of the invention, there may be provided an implantable device, the device having a first bone-facing surface and an opposed second bone-facing surface and having a central opening extending from the first bone-facing surface to the second bone-facing surface, the device comprising a polymeric component, the device comprising a metallic component, the metallic component and the polymeric component being mechanically connected to each other, wherein the device comprises at one end a post, the post extending along a direction from the first bone-facing surface to the second bone-facing surface, the post adapted to be gripped by an installation instrument, the post having a convex exterior, wherein the post is partially in the metallic component and partially in the polymeric component.

In an embodiment of the invention, there may be provided an implantable device, the device having a first bone-facing surface and an opposed second bone-facing surface and having a central opening extending from the first bone-facing surface to the second bone-facing surface, wherein the device comprises at one end a post, the post extending along a direction from the first bone-facing surface to the second bone-facing surface, the post adapted to be gripped by an installation instrument, the post having a convex exterior, wherein the post comprises flats or corners or both, and wherein the device comprises an engagement feature that is in addition to the post.

In an embodiment of the invention, there may be provided an implantable device, the device having a first bone-facing surface and an opposed second bone-facing surface and having a central opening extending from the first bone-facing surface to the second bone-facing surface, the device comprising a polymeric component and a metallic component that are mechanically joined to each other, the metallic component comprising a substantially solid region and a porous region, wherein one of the bone-facing surfaces that comprises a continuous path of material of the porous region all the way around a circumference of the central opening, and comprises a surface of the polymeric material around a portion of the circumference of the central opening, wherein the porous metal protrudes beyond the polymeric component.

In an embodiment of the invention, there may be provided an implantable device, the device having a first bone-facing surface and an opposed second bone-facing surface and having a central opening extending from the first bone-facing surface to the second bone-facing surface, wherein the device comprises a first metallic component, a second metallic component, a first side polymeric component and a second side polymeric component, wherein the first metallic component is mechanically joined to the first side polymeric component and to the second side polymeric component, and the second metallic component is mechanically joined to the first side polymeric component and is mechanically joined to the second side polymeric component.

BRIEF DESCRIPTION OF THE ILLUSTRATIONS

Embodiments of the invention are further described but are in no way limited by the following illustrations.

FIG. 1B shows the implant of FIG. 1A viewed mostly from the side, with localized views of some height interrelationships.

FIG. 2A is a three-dimensional view showing an implant suitable for insertion via an oblique approach.

FIG. 2B shows the implant of FIG. 2A in a view looking approximately horizontally at the longer side of the implant.

FIG. 2C shows the implant of FIG. 2A in a view looking approximately horizontally at the leading end of the implant.

FIG. 2D is similar to FIG. 2C except at a slightly different viewing angle.

FIG. 2E is shows the implant of FIG. 2A looking partly at the end that is suitable to be grasped by an installation instrument, i.e., the end opposite the end shown in FIGS. 2C-2D, but also showing some of the side of the implant.

FIG. 2F shows the polymeric component of the implant of FIG. 2A.

FIG. 2G shows the non-polymeric components of the implant of FIG. 2A.

FIG. 2H shows another view of the trailing end component of the implant of FIG. 2A.

DETAILED DESCRIPTION OF THE INVENTION

Figure 1A:
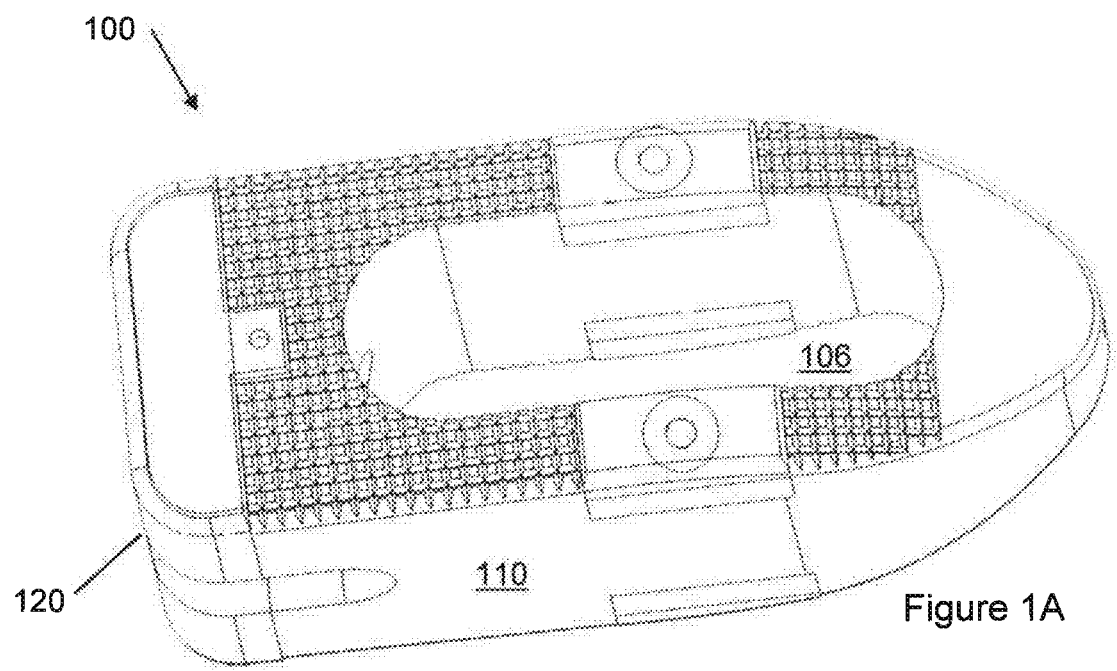
FIG. 1A is a three-dimensional view showing an implant suitable for Posterior Lumbar Interbody Fusion.

Reference is now made to FIGS. 1A-7E. In an embodiment of the invention, the anatomy may have a caudal-cephalad direction, and an anterior-posterior direction and a lateral direction. The anterior-posterior direction may be generally perpendicular to the cephalad-caudal direction. Also, the lateral direction may be generally perpendicular to the cephalad-caudal direction. Extending along the cephalad-caudal direction of the implant, there may be an open channel therethrough intended for bone to grow into and through along the cephalad-caudal direction connecting the respective vertebrae.

Generic Components and Features

In an embodiment of the invention, the implant may have one or more components that are made of a polymer. A polymer often used in implants, which has both biocompatibility and good structural strength, is polyetheretherketone (PEEK). PEEK has an elastic modulus that is reasonably close to the elastic modulus of natural bone, which helps to avoid the problem of stress shielding. PEEK can be considered to be inert with respect to bodily fluids and osseointegration. A further possibility is the use of PEEK that contains granules or particles of an osseointegrative material such as hydroxyapatite (HA). HA is a component of natural bone and is osteoconductive. HA enhanced PEEK has osseointegration properties that are superior to those of pure PEEK. Both PEEK and PEEK HA Enhanced are commercially available (as PEEK-Optima and PEEK-Optima HA Enhanced, respectively) from Invibio (West Conshohocken, Pa.). Another such material is available from DiFusion Technologies (Georgetown, Tex.). In general, osseointegrative materials that could be used include hydroxyapatite, bioactive glass, and any of the various chemical or crystallographic forms of calcium phosphate.

In embodiments of the invention, the polymeric component may have engagement features that are truncated pyramids or pyramids, or may have engagement features that are grooves or ridges that extend in an extruded manner along one direction of the polymeric component. It is also possible to have both pyramids and grooves, or still other shapes, as engagement features. The engagement features of the polymeric component may be suitable to resist motion or expulsion of the implant from its implantation site. The dimensions such as height (peak to valley) or dimension perpendicular to the local implant surface may be in the range of 0.2 mm to 2 mm. Such dimension of the grooves or ridges or truncated pyramids or similar feature may be larger than the dimension of porosity or roughness of the porous region (if such a region exists) of the metallic component, and may be larger in general than whatever roughness or surface finish exists on any portion of a metallic component of the implant. In an embodiment of the invention, the pyramids are spaced in a pattern of a grid whose spacing or dimensions of repetition of repeating features is 0.5 mm. More generally, the spacing or dimension of repeating pattern may be 0.2 mm to 2 mm. The ratio of feature height to the repeating pattern dimension may be in the range of 0.5 to 2.

In an embodiment of the invention, the implant may have components that are made of metal. Metals, such as titanium and its alloys, have advantageous properties of strength and biocompatibility, although in some applications their elastic modulus is so much greater than the elastic modulus of natural bone that there can be a stress shielding problem. In any one or more or all of the metallic components, the metal may comprise a region that is a substantially solid metal and another region that is a porous construct of the same metal as the solid region. Such regions may be joined to each other or may be formed integrally with each other. Porous metal, especially porous metal that is titanium or titanium alloys, is considered to have good osseointegrative properties. Solid metal is generally considered to have good strength and toughness, among other properties. A substantially-solid region may be considered to be a region that has a density that is greater than 90% of the theoretical solid density of the same substance. In the porous region, it is typical that the porosity of the porous region might be about 50%/o, or more generally the density of the porous region may be between 40% and 80% of the theoretical solid density of the same substance. A typical pore size in the porous region may be between 100 microns and 700 microns. All of the pores may be in such size range, or a majority of the pores may be in such size range. Dimensions of surface roughness of the porous region may be similar to the pore size dimensions. Pores may be open pores, i.e., connected with each other, although they do not have to be.

The roughness of the bone-facing surface of the polymeric component can be rougher or larger than the roughness of the metallic component, which may have some or all of its bone-facing surface being porous. This comparison can be judged using the maximum-to minimum (peak-to-valley) height dimension of features in the surface of the polymeric component, and using pore size of the porous region in the metallic component, or other appropriate descriptor of the properties of the bone-facing surface of the metallic component. The pore size of the porous region of the metallic component may, for example be in the range of from 100 microns to 700 microns. This may be determined by the particle sizes in the metal powder initially used in a manufacturing process, the processing parameters during additive manufacturing, and other variables. The features in the polymeric part may be machined, for example. The maximum-to minimum (peak-to-valley) height dimension of features in the surface of the polymeric component may be in the range of from 0.2 mm to 2 mm. Even though some part of that possible range may overlap with the overall possible range of pore sizes in porous metal, it still may be provided, in a particular implant design, that all of the polymeric features are larger than the pore size in the porous metal of that particular implant.

Formation of a metallic component that is substantially solid in one region and porous in another region may be performed using an additive manufacturing technique in which particles of powder are joined to other particles to form an object. Such joining can be performed by selective laser sintering, by electron beam, or by other methods. Powder-based technologies include selective laser sintering (SLS), direct metal laser Sintering (DMLS), selective laser melting (SLM), and Electron Beam Melting (EBM). Some of these use concepts comparable to the SLS except that the material is fully melted rather than sintered. The degree of porosity in any localized place may be controlled, at least in part, by the amount of energy deposited at a particular location such as using the laser beam or electron beam. It is possible to cause sintering in locations that are desired to be porous, and to cause melting followed by re-solidification in locations that are desired to be substantially-solid, or to cause varying degrees of sintering in various locations. These choices can be made by adjusting the amount of local energy deposition. It might also be possible to use three-dimensional printing onto a powder bed with drops of binder liquid, followed by sintering.

Embodiments of the invention may comprise metallic components in which there are provided certain features such as through-holes for screws that are intended to engage with bone, backout-prevention devices for securing those screws, holes for press-fit pins therethrough, and features that interface with an instrument that is used during insertion of the implant at a surgical site. Such features may be located entirely or primarily in regions of the metallic component that are substantially solid metal regions, rather than porous. Regions that are made of substantially solid metal can be expected to have greater mechanical strength than regions that are made of porous metal. Also, for purposes such as press-fits, regions that are made of substantially solid metal may have good dimensional accuracy and stability such as for dimensions of hole diameters, in comparison to similar geometries if such features were to be produced in porous metal, although it is not wished to be bound by this theory.

A polymeric component and a metallic component may be mechanically joined to each other as described elsewhere herein.

In an embodiment of the invention, when the components are fully assembled to each other, the metallic component may protrude to a greater height toward the bone that the bone-facing surface faces, generally along the longitudinal (cephalad-caudal) direction, than nearby components such as a polymeric component. That amount of protrusion by which the metallic surface protrudes relative to a nearby or adjacent polymeric surface may be about 0.25 mm, or more generally, in the range of 0.1 mm to 2 mm. If such nearby or adjacent surface, such as of a polymeric component, is corrugated or irregular, such protrusion may be measured relative to an enveloping surface that contacts peaks of the corrugated or irregular surface. This is illustrated in FIG. 1B.

Relative positions of components can be defined using a polymeric region bounding plane that is a best-fit to local peak features of the polymeric component. For a metallic component, relative positions of components can be defined using a metallic region bounding plane that is a best-fit to local peak features of the metallic component. The quantity of such local peak features can be, four example, three or four such peak features counted along the external surface of the component in a direction toward or away from the interface between the polymeric component and the metallic component. A similar method may be used in regard to a bounding plane for features in the polymeric component.

The metallic component may have a porous metal region that is external or bone-facing. Either all or some of the external or bone-facing surface may be porous. The overall geometry of the metal surface may be such that the scale of roughness or porosity of the metal surface, if any, is smaller than the scale of roughness or dimensions of features of the polymeric surface that is bone-facing adjacent to the metal surface.

In the polymeric component, the polymeric surface or the bulk polymeric material, or both, may contain inclusions of hydroxyapatite or other osteoconductive or osseointegrative material. The inclusions at the surface may be exposed at surfaces as a result of the initial process of manufacturing the polymeric material, or they may be exposed by machining or other material removal process subsequent to initial manufacturing of the polymeric material.

In an embodiment of the invention, attachment of a metallic component to a polymeric component may be done using a pin whose direction is generally parallel to the longitudinal (cephalad-caudal) direction of the implant. In such a situation, load in a longitudinal direction that is transmitted from the metallic component to the polymeric component may be transmitted by direct contact of surfaces that are somewhat perpendicular to the direction of the force. It is possible for load to be transmitted by direct bearing of a surface of the metallic component bearing against a surface of the polymeric component. In such a situation, the pin may serve a function of establishing location. The pin may also serve to maintain various parts in assembled relation to each other.

An embodiment of the invention can comprise a metallic component that has at least one substantially-solid region and at least one porous region. It is possible that the porous region can be exposed on an exterior-facing surface of the metallic component, and only on an exterior-facing surface of the metallic component. It is possible that substantially-solid region can be exposed on surfaces other than the exterior-facing surface of the metallic component, and also can be exposed on the exterior-facing surface of the metallic component surrounded by porous region, and can be exposed on the exterior-facing surface of the metallic component surrounding the porous region. It is possible that the surface of the metallic component that is in contact with the polymeric component may entirely be substantially-solid metal. It is possible that the surface of the metallic component that is in contact with the polymeric component may be a majority of substantially-solid metal.

In an embodiment of the invention, the implant may have a central hole extending therethrough from a first bone-facing surface to a second bone-facing surface, with the implant forming a closed path around the central hole. Proceeding around the closed path at a bone-facing surface, that is, the bone-facing superior surface or the bone-facing inferior surface of the wall, there may be alternating regions of polymeric material and metallic material. Proceeding around the closed path at a bone-facing surface, there may be a region that is entirely polymeric at the bone-facing surface, followed by a region that is entirely metallic at the bone-facing surface, followed by a region that is entirely polymeric at the bone-facing surface. Proceeding around the closed path at a bone-facing surface, there may be a region that is entirely metallic at the bone-facing surface, followed by a region that is entirely polymeric at the bone-facing surface, followed by a region that is entirely metallic at the bone-facing surface. In connection with some of the described geometries and implants, at the midplane of the implant, proceeding around the closed path, there may be a continuous path of polymeric material.

In embodiments of the invention, the bone-facing surface may comprise polymeric material and a porous region of a metallic component and a substantially-solid region of a metallic component. The polymeric material may comprise particles or inclusions of an osteoconductive material.

In embodiments of the invention, the implant could have a metallic end component joined to a polymeric component in such a way that at some portions of the external perimeter of the implant, there is only metal, no polymer. The metallic end component could have features such as teeth to interface with an instrument, holes to interface with an instrument, threads to interface with an instrument, holes for bone screws, holes for other screws, and other features. The metallic end component could comprise both a substantially-solid region and a porous region. The metallic end component and the polymeric body could be joined by a press-fit pin similar to what is described herein for other purposes. There may be a relationship between the end component and the polymeric component such that when the end component and the polymeric component are assembled to each other even without pins, there is some constraint on their relative motion.

Embodiments of the invention are further described with respect to certain specific configurations of spinal implants.

PLIF Implant

Referring now to FIGS. 1A-1I, in an embodiment of the invention, there may be provided an implant 100, which may be suitable for implantation by a Posterior Lumbar Interbody Fusion (PLIF) surgical approach. Such an implant 100 may comprise a polymeric component 110 and metallic components in the arrangement shown.

Figure 1C:
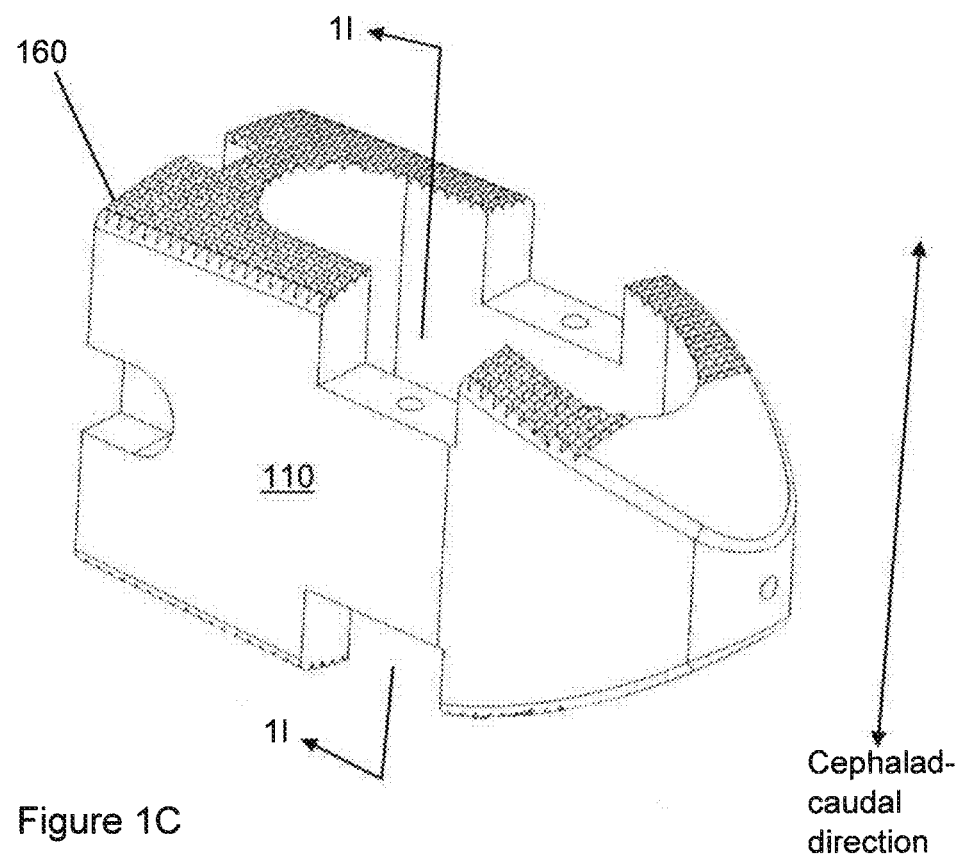
FIG. 1C shows the polymeric component of the implant of FIG. 1A.
Figure 1D:
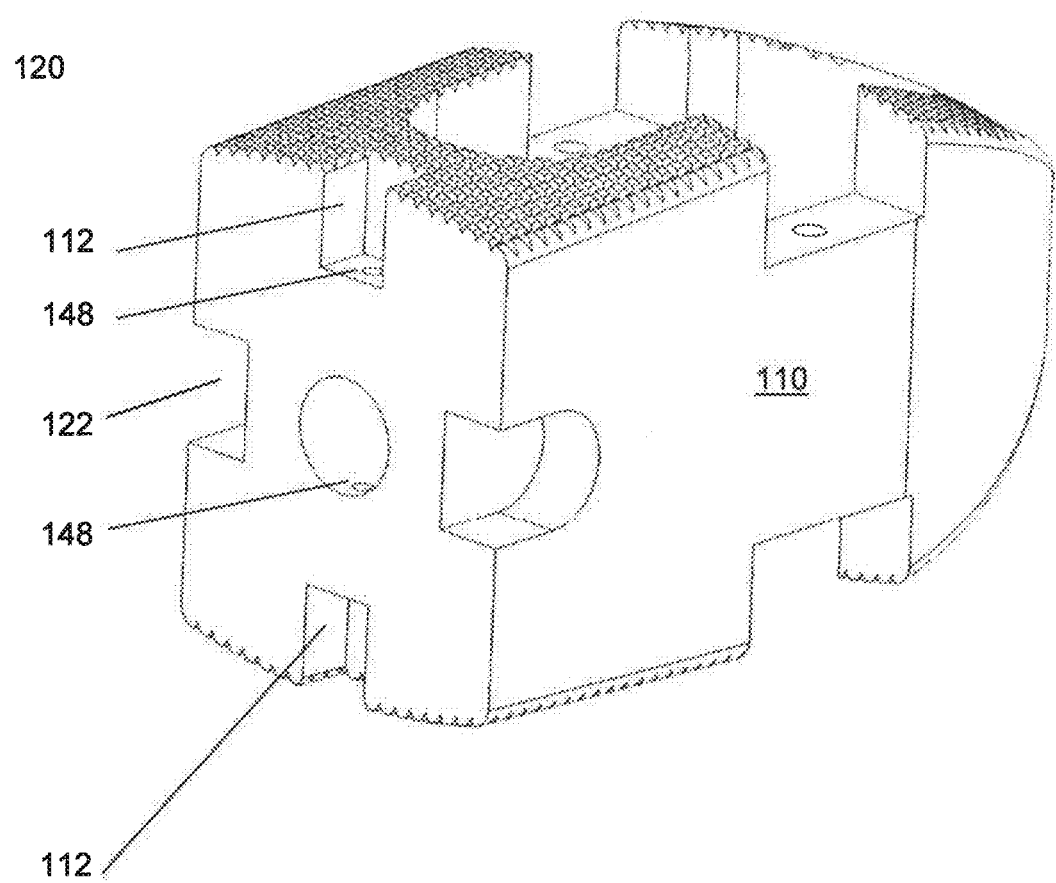
FIG. 1D shows another view of the polymeric component of FIG. 1A.

FIG. 1A shows the PLIF implant 100 including all of its components assembled to each other. The implant may have a first bone-facing surface and a second bone-facing surface opposed to the first bone-facing surface, and may have a central opening or passageway 106 therethrough from the first bone-facing surface to the second bone-facing surface. FIG. 1C shows the polymeric component 110 only. In FIG. 1D the polymeric component is omitted, and all other components are shown.

As illustrated in FIG. 1C-1D, there may be a polymeric component 110 that may make up a majority of the implant 100. The polymeric component 110 may exhibit a continuous path of polymeric material, at least on the interior of the central opening or passageway 106 through the implant 100 extending around the interior surface of central hole 106, although there may be localized cutouts. Furthermore, at one end of the implant 100 there may be a trailing end component 120 that is a metallic component. The term trailing end may refer to a particular end that is not the end that initially enters the surgical site, but rather is the end of the implant that is engaged with an installation instrument. The opposite term, referring to the end that enters the surgical site first, is leading end. The trailing end component 120 may have upper and lower protrusions 130, and the polymeric component 110 may have upper and lower recesses 112 dimensioned so as to be able to receive the respective protrusions 130. Furthermore, the protrusions 130 may have holes 132 therethrough that are suitable to receive pins 134. The polymeric component 110 may have a hole(s) 148 also suitable to receive pins 134 when the various parts are in an assembled configuration. The pins 134 may have a press-fit relation with at least some of these components.

Figure 1E:
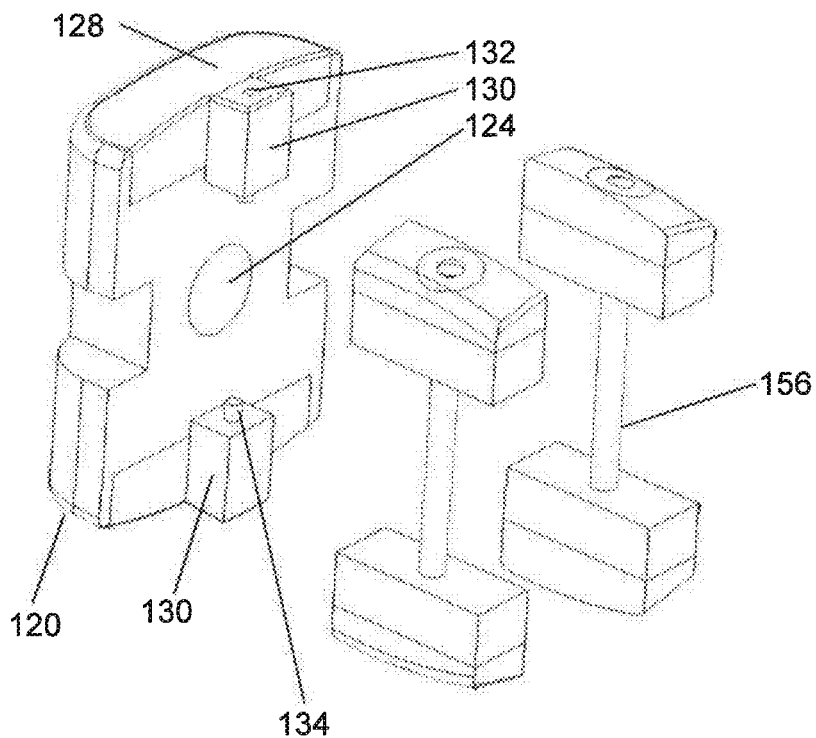
FIG. 1E shows the non-polymeric components of the implant of FIG. 1A.
Figure 1F:
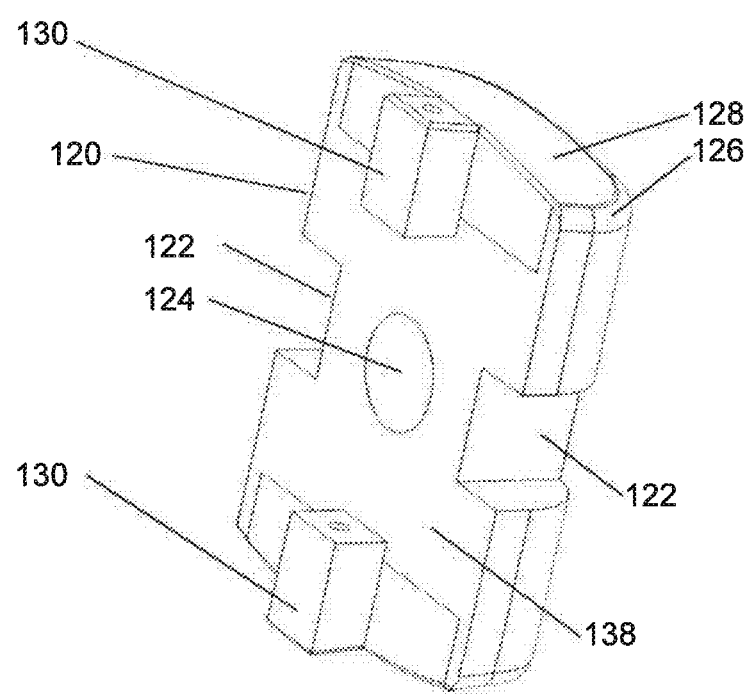
FIG. 1F shows the end component of the implant of FIG. 1A, from a perspective different from the perspective of FIG. 1E.

As shown in FIG. 1E and separately in FIG. 1F, there may be a trailing end component 120, which may be made of metal. Some of the end component 120 may be solid metal and other portions of the end component 120 may be porous metal. Trailing end component 120 may have recesses 122 on its sides that may be suitable to engage with an installation instrument (not illustrated). Trailing end component 120 may also have a central hole 124 that is suitable to engage with an installation instrument (not illustrated). Central hole 124 may be threaded. Trailing end component 120 may have substantially-solid region 126 and porous region 128. Trailing end component 120 may have protrusions 130, which may be generally rectangular blocks (parallelepipeds) that protrude from a generally flat surface 138 of the end component 120. The protrusions 130 may be made of substantially-solid material. Some part of the protrusions 130 may be continuous with substantially-solid material in other parts of the end component 120. The protrusions 130 also may be connected to or continuous with the porous region 128. As illustrated, the protrusions 130 may be connected to or continuous with both the substantially-solid region 126 and the porous region 128. The protrusions 130 may have therein holes 132 suitable to receive pins 134, which may form a press-fit. FIG. 1E shows pins 134 engaged with protrusions 130, while FIG. 1F does not show those pins. End component 120 may also have surface 138 that faces a corresponding surface on polymeric component 110.

As can be seen in FIGS. 1D-1F, there may be a relationship between the polymeric component 110 and end component 120 such that when polymeric component 110 and end component 120 are in their assembled relation to each other even if pins 134 are not present, there are constraints on possible motion between polymeric component 110 and end component 120. As illustrated, when polymeric component 110 and end component 120 are in their assembled relation to each other, essentially the only degree of freedom of motion that is permitted is translation along the long direction of the implant 100, which is a direction of motion that is used in assembling the end component 120 to polymeric component 110 and that would cause shear of pins 134 if pins 134 were in place. Because of the interrelationships between protrusions 130 and recesses 112, there may be constraint against relative motion of the two parts along the direction of pins 134. As a result of such constraint, it is sufficient if pin 134 forms a press-fit in only one of the two components 110, 120; it is not necessary for a press-fit to exist between pin 134 and both polymeric component 110 and end component 120. For example, a press-fit might be created between pin 134 and end component 120, while there may be a looser fit relationship between pin 134 and polymeric component 110. The opposite relationship is also possible. Such provision of a press-fit relationship at less than all of the interfaces of pin 134 may be helpful in reducing the amount of insertion force that is needed to insert pin 134 (which is of somewhat small diameter and might be susceptible to buckling).

Figure 1G:
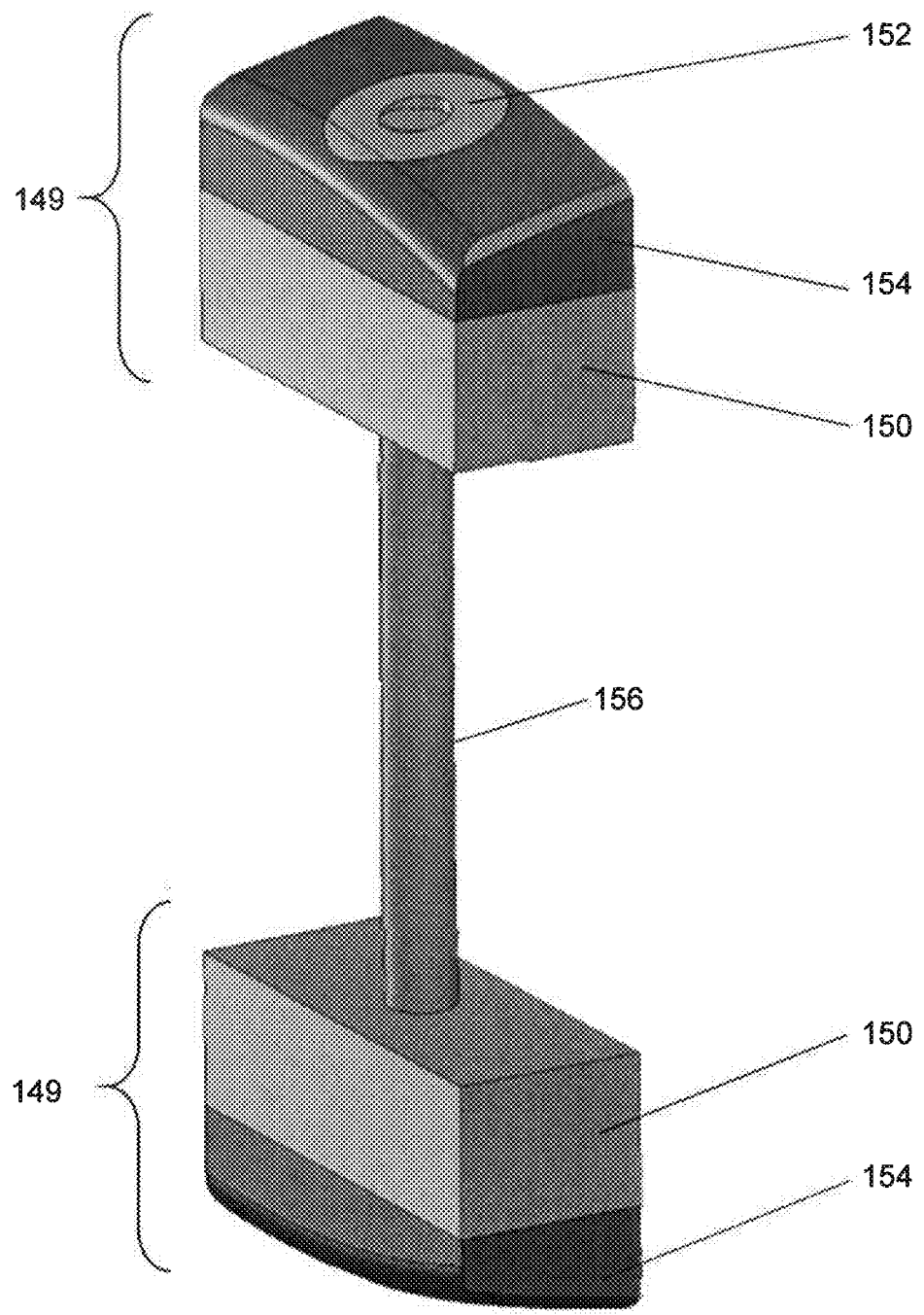
FIG. 1G shows two pads connected by a pin.
Figure 1H:
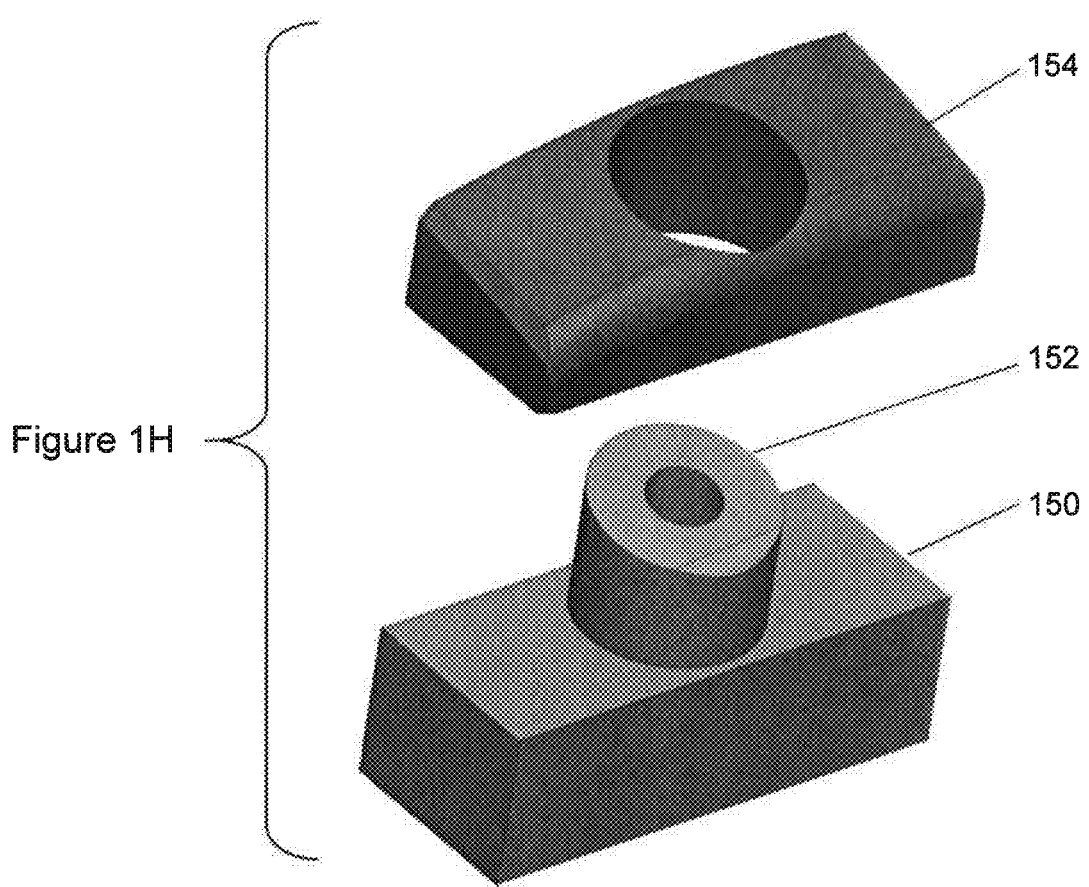
FIG. 1H is an exploded view of the metallic pad, in which the porous portion and the substantially-solid portion are shown separated from each other.
Figure 1I:
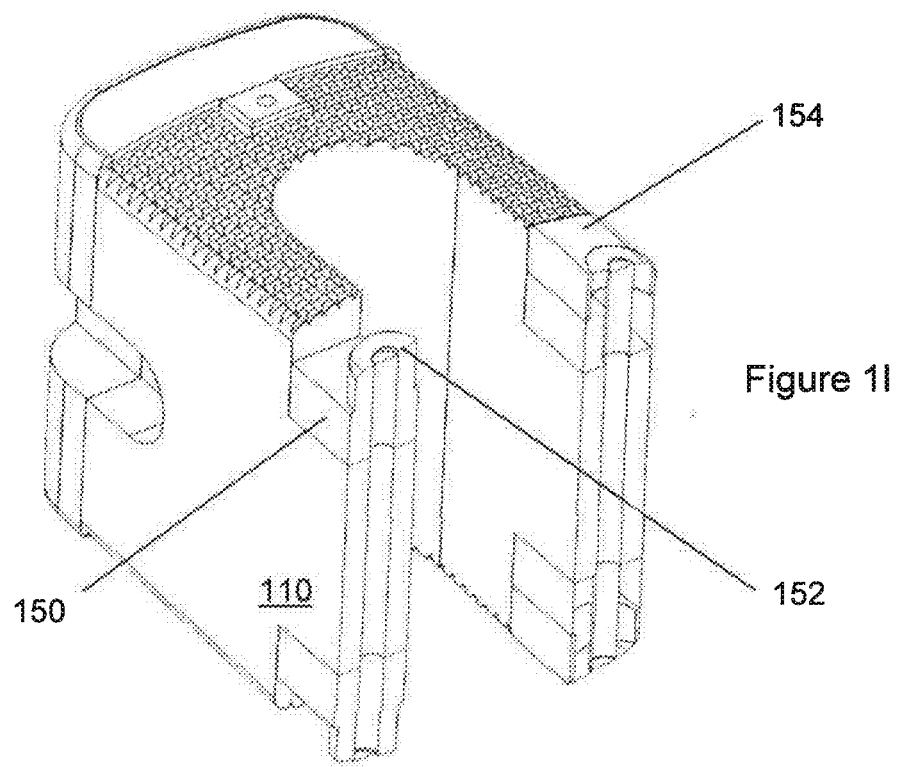
FIG. 1I is a cross-section showing the holes associated with the "barbell" construct.

Referring now to FIGS. 1G-1I, there may also be provided metallic components in the form of pads 149 that are exposed on bone-facing superior and inferior surfaces of the implant 100. The metallic components that are pads 149 may have substantially-solid regions 150 and 152, and porous regions 154. Substantially-solid regions 150 and 152 may be connected to each other or integral with each other. As illustrated, substantially-solid region 152 may be surrounded by porous region 154. Such relation may be annular, with substantially-solid region 152 being inside and porous region 154 being outside. Porous region 154 may also contact substantially-solid region 152, with an interface that may be a flat interface.

As illustrated, the metallic components may contain a substantially-solid region 150, 152 and a porous region 154, as discussed herein. As illustrated, in the metallic component that is pad 149, the material that is in contact with the pin 156 to form the press-fit is entirely substantially-solid material, even though other portions of the metallic component are porous regions 154. It is believed that having the material immediately adjacent to the press-fitted pin 156 be substantially-solid material may be advantageous for achieving an accurately-dimensioned and tightly-fitting press-fit, although it is not wished to be limited to this explanation.

Referring to FIG. 1G-1I, in further detail, there is shown a metallic component which is a pad 149 as previously illustrated in FIGS. 1A, 1E. In FIG. 1H the porous region 154 and the substantially-solid region 150, 152 are shown separated or exploded from each other. As illustrated, the porous region 154 and the substantially-solid region 150 have a flat interface with each other, with the interface plane being generally horizontal. It is further illustrated that in the bone-facing portion of the pad 149, the porous region 154 surrounds the substantially-solid region 152. As illustrated, there is a contact interface between the porous region 154 and the substantially-solid region 152 both in one plane (the plane that is horizontal) and in a second plane that is generally perpendicular to the first plane. As illustrated, the second plane is any plane that is tangent to the cylindrical interface between the porous region 154 and the substantially-solid region 152. An annular, or partial-annular, relationship between porous region 154 and substantially-solid region 152 is also possible. Other configurations are also possible.

Superior and inferior metallic components in corresponding places may be connected to each other by a pin 156, which may be press-fit in at least some of components that it passes through. Pin 156 may be a press-fit in a hole through substantially-solid regions 150, 152. Press-fit considerations are discussed elsewhere herein. The two metallic components (pads 149) and the pin 156 that connects them may, in combination, form what may be termed a "barbell" construct. FIG. 1G shows the "barbell" construct in isolation, showing an upper metallic component (pad 149) and a lower metallic component (pad 149) and the pin 156 connecting them.

As an example of engagement features in the polymeric component 110, peaks 160 may be provided in the polymeric component 110. The peaks 160 may be in the form of pyramids or truncated pyramids, or other shapes. The peaks 160 may be configured in a pattern that is a rectangular grid having principal axes that are orthogonal to each other. One of the principal axes of the grid may be parallel to a principal axis of the overall implant 100. One of the principal axes of the grid may be perpendicular to a principal axis of the overall implant 100. Yet another possibility is that engagement features may be ridges that extend for some distance in one direction. It would also be possible to use a combination of ridges and pyramids or truncated pyramids, or still other shapes or combinations thereof.

Referring now to FIG. 1B, it is illustrated that at the bone-facing surface of implant 100, the metallic components such as end component 120 or pad 149 may protrude from implant 100 more prominently than the surface of the polymeric component 110. The metallic components may protrude to a greater height toward the bone that the bone-facing surface faces, generally along the longitudinal (cephalad-caudal) direction, than nearby components such as polymeric component 110. The difference, which is labeled in FIG. 1B, may be in the range of 0.1 mm to 1 mm., typically 0.25 mm.

Oblique Implant

Referring now to FIGS. 2A-2H, there is illustrated an oblique implant 200. In some respects, an oblique implant 200 may resemble the just-described PLIF implant 100. By analogy with other embodiments described herein, oblique implant 200 can have central opening or passageway 206, polymeric component 210, recesses 212, trailing end component 220, recesses 222, central hole 224, substantially-solid region 226, porous region 228, protrusions 230, holes 232, pins 234, solid regions 250 and 252, porous region 254, and pins 256.

In oblique implant 200, polymeric component 210 may contain a pattern of peaks 260. The peaks 260 may be in the form of pyramids or truncated pyramids. The peaks 260 may be configured in a pattern that is a rectangular grid having principal axes that are generally orthogonal to each other. In an oblique implant 200, it is possible that none of the principal axes of the grid pattern of the peaks 260 may be parallel to any principal axis of the overall oblique implant 200. Also, it is possible that none of the principal axes of the grid pattern of the peaks 260 may be perpendicular to any principal axis of the overall oblique implant 200 in the plane of the surface of the implant. This is illustrated in FIG. 2A.

As illustrated especially in FIG. 2B-2D, the implant 200 can have a lordosis angle, i.e., if one views along the long horizontal direction of the implant 200, one of the walls is taller than the opposite wall. Also, as visible in such a view, the slope of the superior or inferior surface of one wall and the slope of the superior or inferior surface of the other wall may both be non-horizontal. Also, as visible in such a view, the slope of the superior or inferior surface of one wall can be different from the slope of the superior or inferior surface of the other wall. As a result, the metal pad 249 on one side of the implant 200 is shown as having a flat surface that is oriented differently from the corresponding flat surface of the metal pad 249 on the other side of the implant 200. Also, as illustrated, along the longer direction of the walls, the implant 200 has some curvature of its bone-facing surfaces.

TLIF Implant

Referring now to FIG. 3A-3H, in an embodiment of the invention, there may be provided an implant 300 comprising a polymeric component and metallic components in the arrangement shown. Such device may be suitable for a TLIF surgical approach (Transforaminal Lumbar Interbody Fusion). In some respects, such an implant 300 may share certain features with the already-described PLIF implant 100. In other respects, unlike the PLIF implant 100, the TLIF implant 300 may have an overall shape that is a generally-curved (banana) shape. Such an implant 300 also may have certain specialized features regarding interface with an installation instrument, and may have certain other features relating to assembly of its components.

The TLIF implant 300 may have a central opening 306 therethrough along a cephalad-caudal direction. The TLIF implant 300 may have an end component 320 that may be metallic. The end component 320 may be suitable to join to polymeric component 310.

Figure 3A:
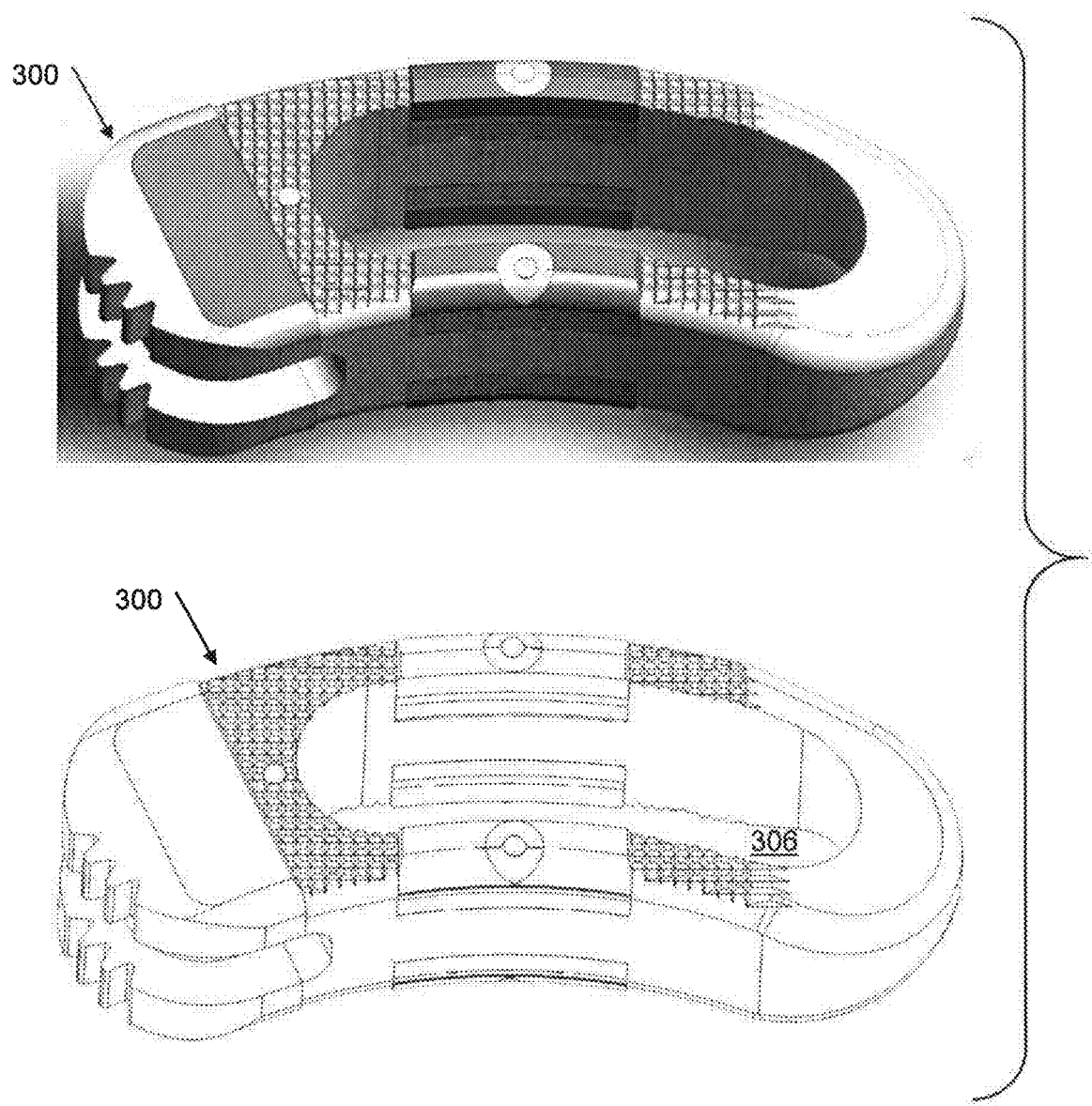
FIG. 3A is a three-dimensional view of an implant suitable for Transforaminal Lumbar Interbody Fusion.
Figure 3B:
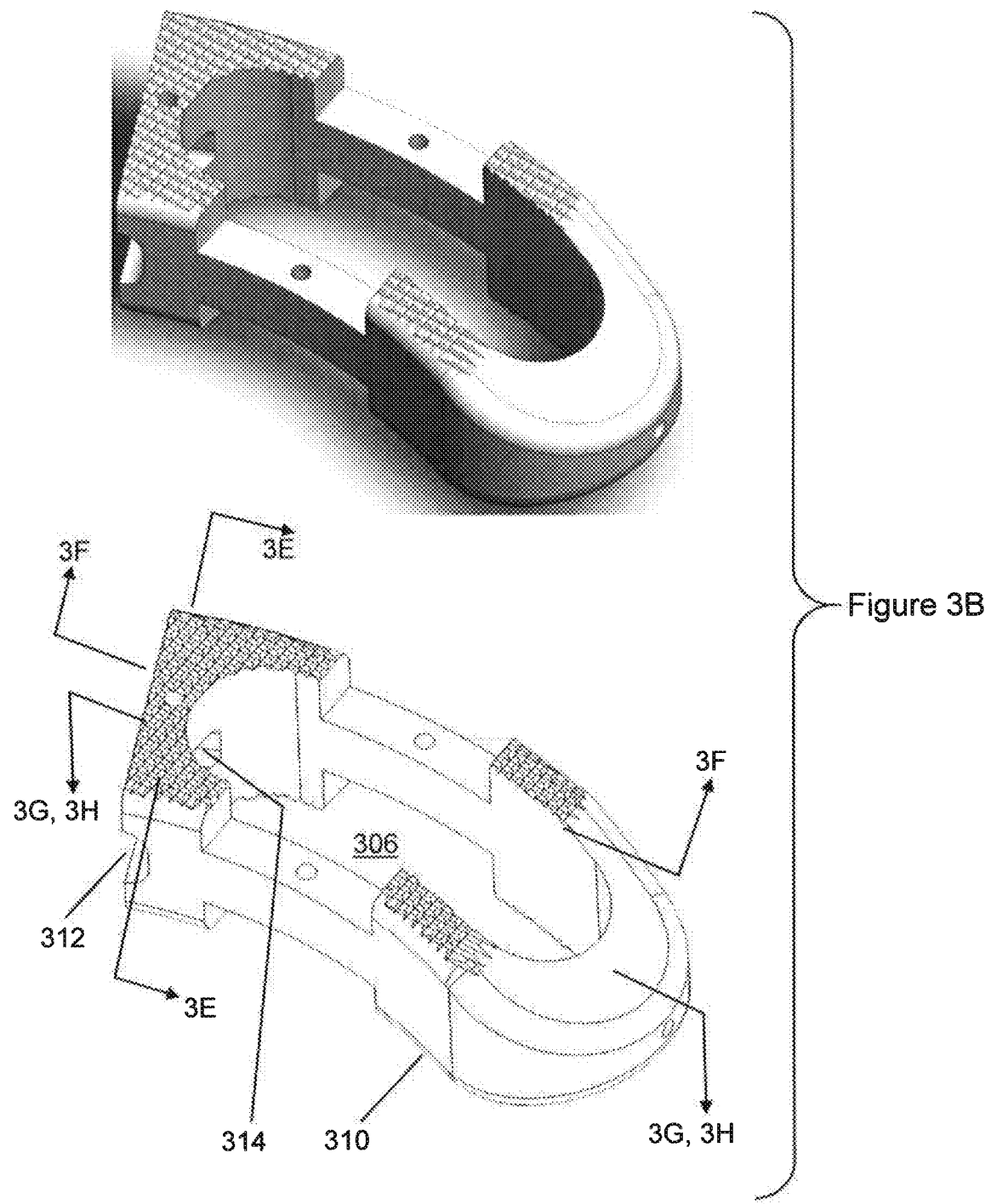
FIG. 3B shows the polymeric component of the implant of FIG. 3A.
Figure 3C:
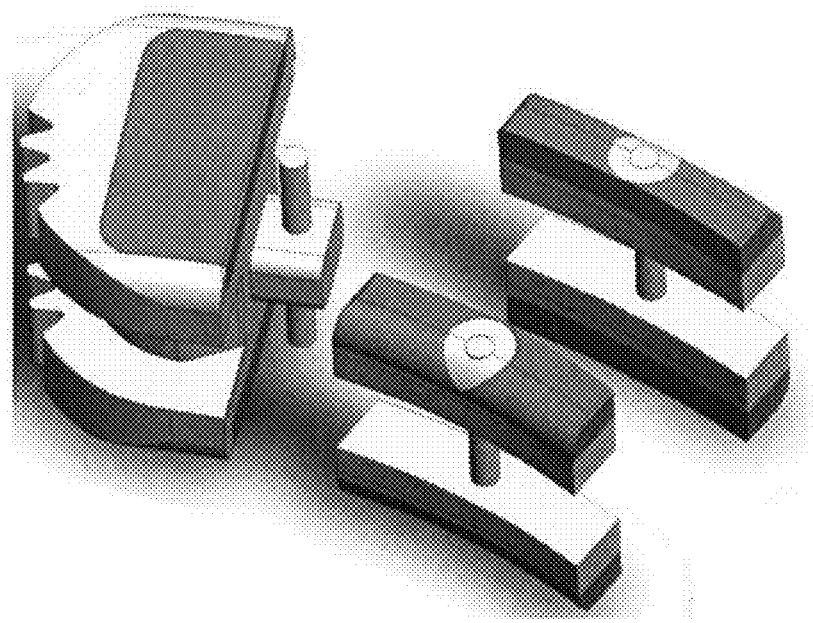
FIG. 3C shows the non-polymeric components of the implant of FIG. 3A.
Figure 3C:
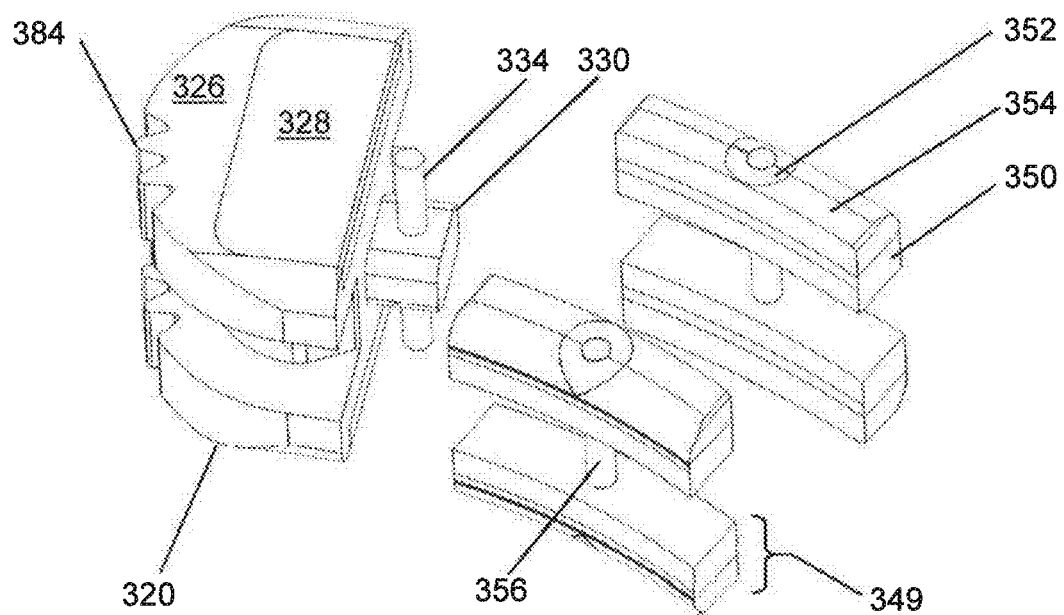
Figure 3D:
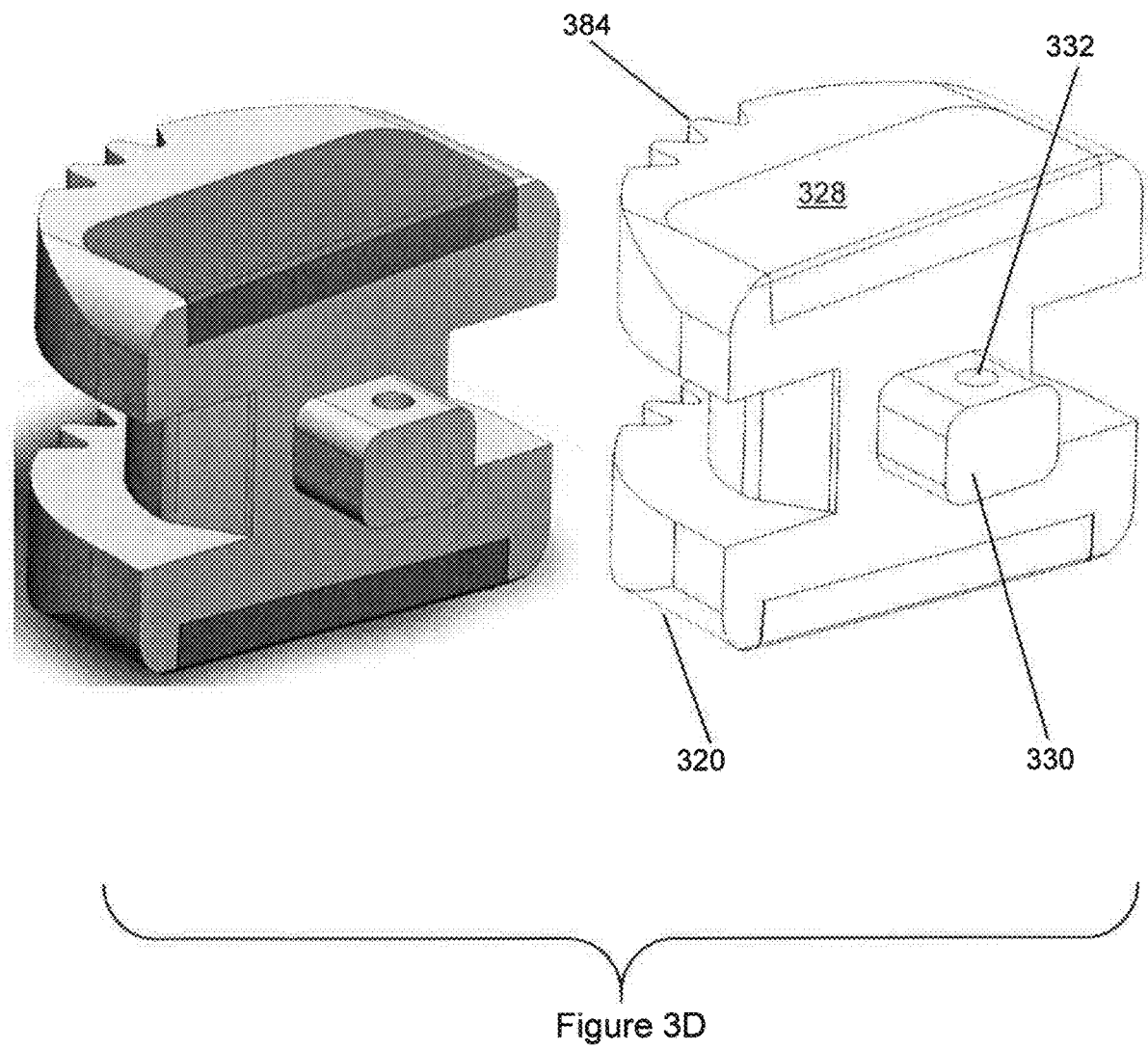
FIG. 3D shows the trailing end component of the implant of FIG. 3A.
Figure 3E:
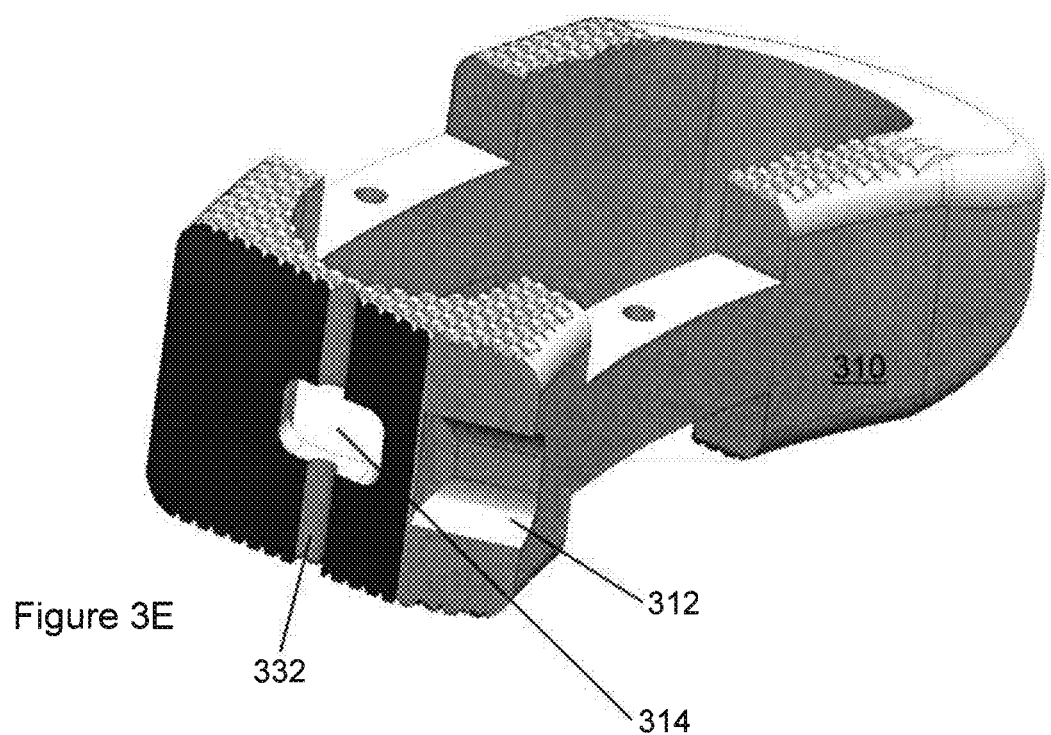
FIG. 3E shows a section of the polymeric component of the implant of FIG. 3A.
Figure 3F:
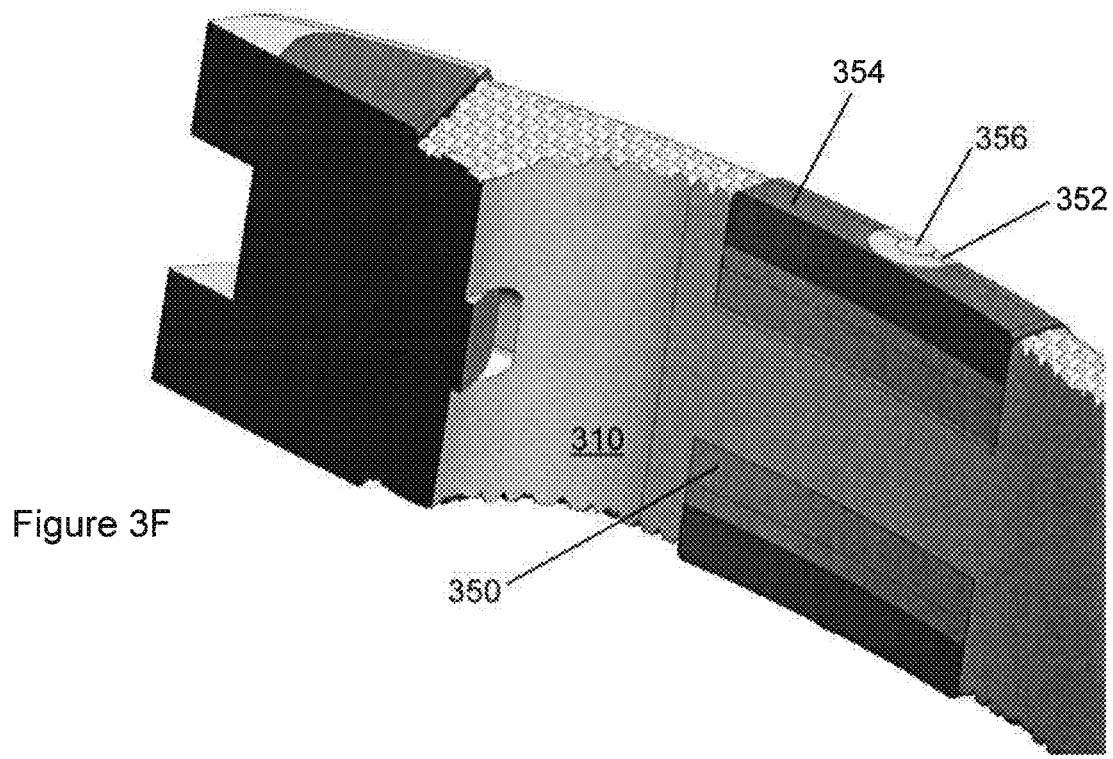
FIG. 3F shows another section component of the implant of FIG. 3A.

FIG. 3A shows the TLIF implant 300 including all of its components assembled to each other. FIG. 3B shows the polymeric component 310 only. In FIG. 3C, the polymeric component is omitted, and all other components are shown. By analogy with other embodiments described herein, TLIF implant 300 can have central opening 306, polymeric component 310, recesses 312, trailing end component 320, recesses 322, central hole 324, substantially-solid region 326, porous region 328, protrusion 330, hole 332, pin 334, solid regions 350 and 352, porous region 354, and pins 356.

The end component 320 may be suitable to be grasped by an installation instrument (not illustrated). Furthermore, there may be provided engagement features 384 such as teeth near an upper surface and a lower surface of the end component 320. The engagement features 384 such as teeth may be suitable to be engaged by a feature of an installation instrument. The end component 320 may comprise a porous region and a substantially-solid region. The porous region 328 of the end component 320 may be bone-facing on both upper (cephalad) and lower (caudal) surfaces of the end component 320.

Furthermore, the end component 320 may have a protrusion 330 that cooperates with the polymeric component 310 to participate in a mechanical connection between the end component 320 and the polymeric component 310. The protrusion 330 may have a hole 332 therethrough generally along the cephalad-caudal direction of the implant 300. The hole 326 may be suitable to receive a pin 334 in a press-fit situation. The protrusion 330 may be made of substantially-solid material, which may be continuous with substantially-solid material in other parts of the end component 320.

Figure 3G:
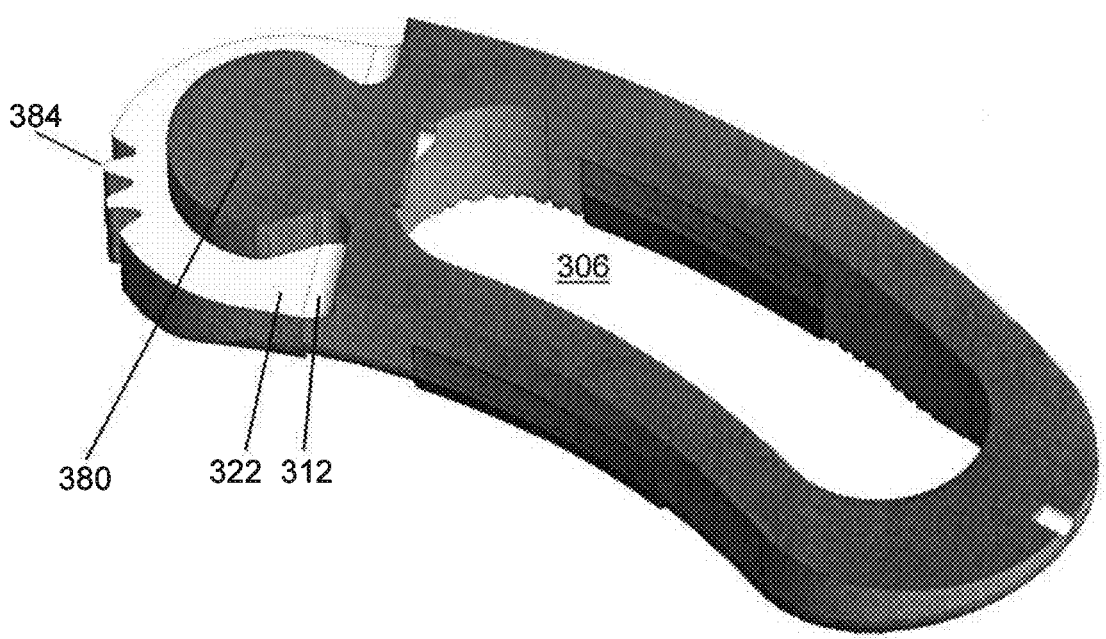
FIG. 3G shows a section through the polymeric component of the implant of FIG. 3A, taken at the midplane.
Figure 3G:
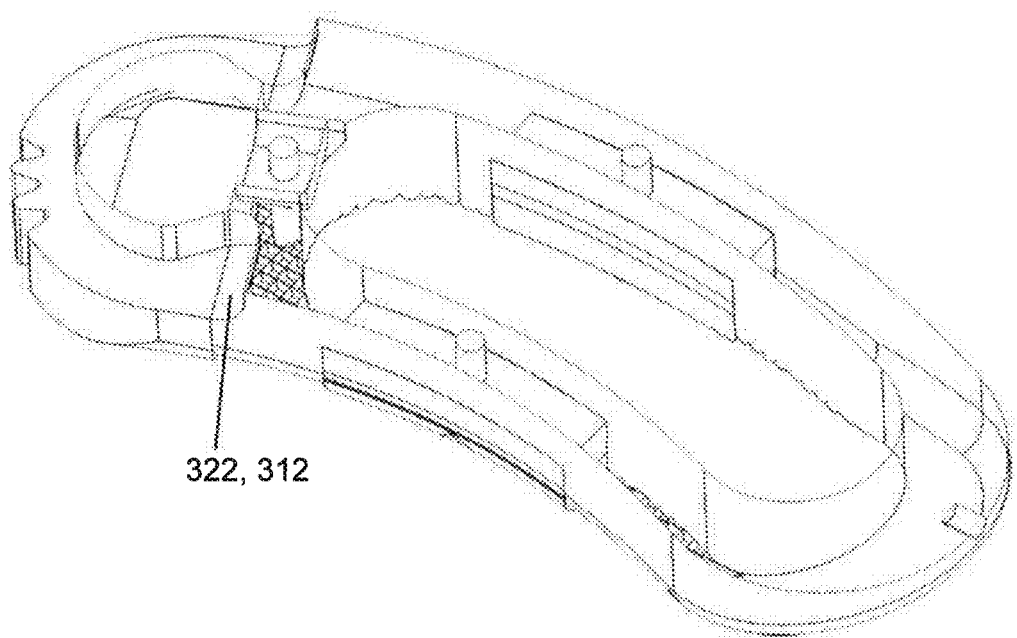
Figure 3H:
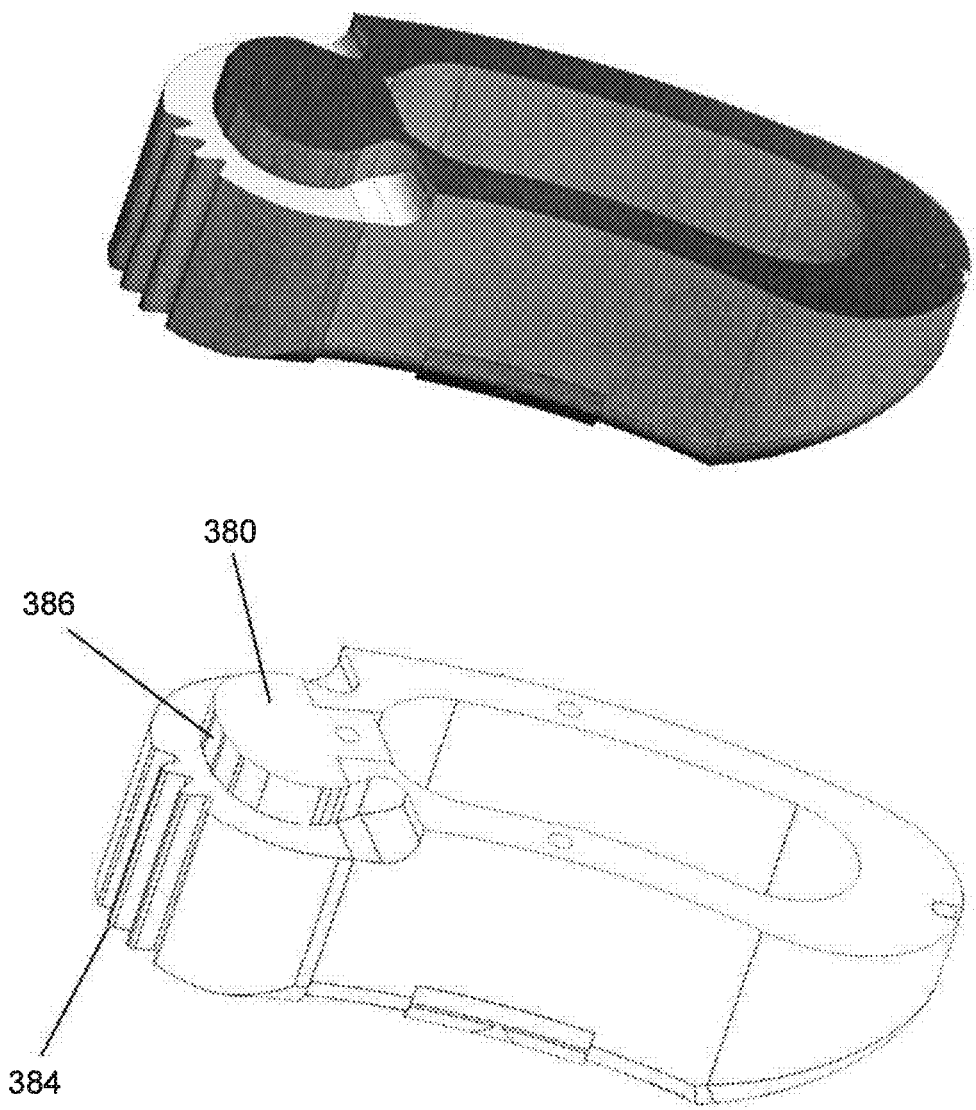
FIG. 3H is similar to FIG. 3G, but with the post shown as having a cross-sectional shape that is polygonal.

Near an end of the implant 300, there may be a defined post 380 that is a portion of a cylinder or prismatic solid, which may amount to more than 180 degrees of external circumference of a cylinder or prismatic solid. The shape of post 380 does not need to be circularly cylindrical everywhere. For example, alternatively the post 380 could be a polygonal prism, or a combination of curved surfaces and prismatic planar surfaces, with any of those shapes or combination of shapes being extruded along the cephalad-caudal direction. The shape or extent of post 380 may be defined in part by a tool-accepting recess 312, 322 in the exterior of the implant 300. The tool-accepting recess may be generally located at or near the midplane of the implant 300. The tool-accepting recess may exist partly (322) in the end component 320 and partly (312) in the polymeric component 310. In FIG. 3G, it can be seen that the void space, which defines the post 380 for gripping by the installation instrument and creates more than 180 degrees of perimeter of the post 380, includes void space in the metallic end component 320 and void space in the polymeric component 310. This allows achieving the desired range of gripping of the post 380, while also achieving the desired proportion of space allocated to the end component 320 and space allocated to the polymeric component 310. The post 380 may be partially in the region of end component 320, which may be metallic, and partially in the polymeric component 310.

The polymeric component 310 may have a protrusion-accepting hole 314, generally in a horizontal direction, suitable to accept the protrusion 330 from the end component 320. The protrusion-accepting hole in the polymeric component may be a through-hole and may have a rounded-rectangle shape. In the polymeric component 310, there may be a pin-accepting hole 332 that intersects the protrusion-accepting hole 314. The pin 334 may have an interference fit relationship with respect to hole 332 in the protrusion 330, and may form a fit that is slightly looser than an interference fit with respect to hole 332 in the polymeric component 310. Alternatively, the opposite situation is also possible.

As can be seen in FIGS. 3B-3E, there may be a relationship between the polymeric component 310 and end component 320 such that when polymeric component 310 and end component 320 are in their assembled relation to each other, even if pin 334 is not present, there are constraints on possible motion between polymeric component 310 and end component 320. As illustrated, when polymeric component 310 and end component 320 are in their assembled relation to each other, essentially the only degree of freedom of motion that is permitted is translation along the direction of the implant 300 that the axis of hole 314, which is a direction of motion that would cause shear of pin 334 if pin 334 were in place. There is constraint against relative motion of the two parts along the direction of pins 334. As a result of such constraint, it is sufficient if pin 334 forms a press-fit in only one of the three interactions with components 310, 320; it is not necessary for a press-fit to exist between pin 334 and both polymeric component 310 and end component 320. For example, a press-fit might be created between pin 334 and end component 320, while there is a looser fit relationship between pin 334 and polymeric component 310 in either or both of the superior and inferior directions. Other fit relationships are also possible as long as there is one press-fit along the length of pin 334. Such provision of a press-fit relationship at less than all of the interfaces of pin 334 may be helpful in reducing the amount of insertion force that is needed to insert pin 334 (which is somewhat narrow and might be susceptible to buckling).

As illustrated, the polymeric component 310 may have recesses suitable to accept metallic components such as pads 349. There may also be provided metallic components such as pads 349, which may comprise both substantially-solid regions 350, 352 and porous regions 354. Opposed metallic components may be connected by a pin 356, which may have a press-fit engagement with the metallic components such as pads 349. In polymeric component 310 there also may be holes joining opposed such recesses, suitable to be occupied by pins 356. Such components and features may be similar to components and features described elsewhere herein in connection with other geometries of implants. This embodiment of implant 300 may have a "barbell" construct as described elsewhere herein in connection with other embodiments.

As discussed elsewhere herein, the metallic components (such as end component 320 and various pads 349) may protrude further toward the bone at the surgical site than the polymeric component 310, while the polymeric component 310 may have a larger dimension of roughness than the metallic components.

The implant 300 may have an indexing feature 384 near post 380. During the process of implantation of implant 300 at the surgical site, the post 380 may be grasped by a grasping feature of the installation instrument, and the indexing feature 384 may be interacted with by a corresponding feature of the installation instrument. The indexing feature 384, in combination with its interaction with the installation instrument, may be such as to define a number of discrete positions as represented by the angle between the implant 300 itself and the shaft of the installation tool. During the process of implanting such an implant at the surgical site, this angle may be changed as a result of actions taken by the surgeon.

In such an implant, as illustrated, there may be provided a superior indexing feature 384 superior of the region of post 380, and an inferior indexing feature 384 inferior of the region of post 380. As illustrated, the indexing features 384 comprise teeth. As an alternative to teeth, it would also be possible to provide other geometric indexing features at desired angular locations. The superior and inferior indexing features 384 are illustrated as being in vertical alignment with each other (along the cephalad-caudal direction of implant 300). The indexing features 384, such as teeth, may be equally spaced with respect to angular position around the axis of post 380, but they do not have to be equally spaced.

In such an implant 300, the post 380 can be described by the shape of its cross-section, which may be a cross-section taken in a plane that is perpendicular to the longitudinal or extruded shape of the post. The longitudinal or extruded direction of the post may correspond to the cephalad-caudal direction of the implant. The cross-sectional shape of the post 380 may be a polygon, which may be a regular (equal-sided) polygon. The polygon may have an even number of sides 386 so that there are parallel sides that can be grasped in opposition to each other. Alternatively, grasping does not have to be by flat parallel surfaces against other flat parallel surfaces, but rather could involve an indented surface of the grasper contacting a corner of a polygonal shape of the post 380, which may involve the grasper contacting both of the polygon sides that meet to form the corner.

The polygon of post 380 may be a regular polygon. It is further possible that the polygon of post 380 might not be a regular polygon and the indexing features 384 such as teeth might not be equally-spaced either. In any such situation (either regular spacing or irregular spacing), the angular locations of the sides 386 of the polygon and the angular arrangement of the indexing features 384 may be coordinated such that when the installation instrument is locked to set a particular angular position with regard to the indexing features 384, a grasping feature of the installation instrument also is suitably positioned to optimally grasp the post 380 such as polygonal sides 386 of the post 380. The relationship between the installation instrument, the indexing features and the post 380 may be such that whenever the installation instrument interacts with the indexing feature to position the implant 300 in one of the discrete positions permitted or encouraged by the indexing feature, the grasping feature grasps features of post 380 in a desired locally-optimum manner of grasping. For example, a desired grasp of post 380 could be a flat surface of the grasping feature in contact with a corresponding flat surface of the post 380. Or, a desired grasp of post 380 could be a grasping surface having an indented shape that contacts a corner and the flats that join to make the corner. Grasping on one side of the post could be either grasping of the flat geometry or grasping the corner geometry, and grasping on an opposite side of the post 380 could be either of the flat geometry or the corner geometry, in any combination.

Furthermore, it is possible that with the engagement feature 384 (such as teeth) having more than one permitted engagement position, there is an engagement angular interval between adjacent ones of the permitted positions. It is further possible that on the post 380 the flats or corners define a gripping angular interval between adjacent ones of the flats or the corners. It is further possible that the engagement angular interval equals the gripping angular interval. In a related approach, it is possible that the gripping angular interval can be an integer multiple of the engagement angular interval, or the engagement angular interval can be an integer multiple of the gripping angular interval. One way that gripping of a polygonal shape can be performed is by flats of the gripper against flat surfaces of the polygon. It is also possible that an indented shape of the gripper can grip some combination of corners and flats.

As described elsewhere herein, the post 380 may be partly made of the metal of end component 320, and partly of polymer of polymeric component 310.

Lateral Implant

Figure 4A:
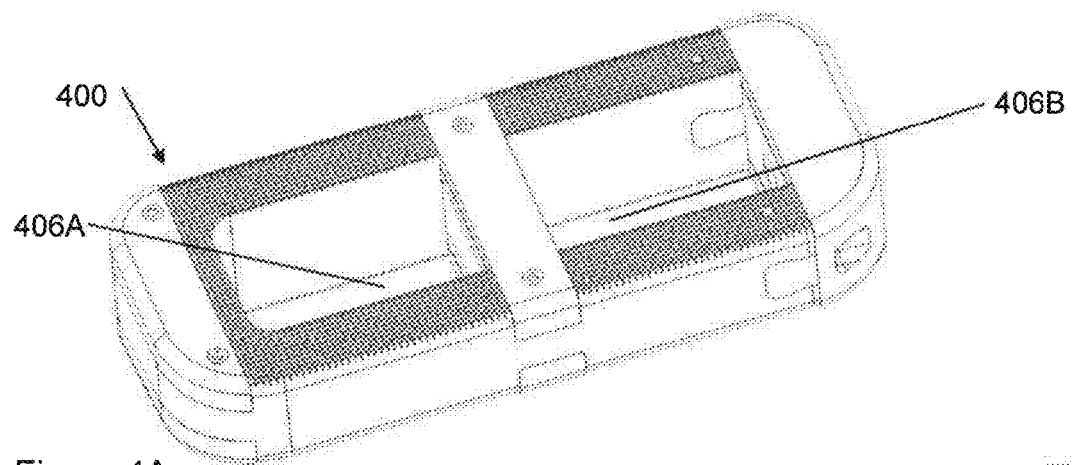
FIG. 4A is a three-dimensional view showing an implant suitable for insertion via a lateral approach.
Figure 4B:
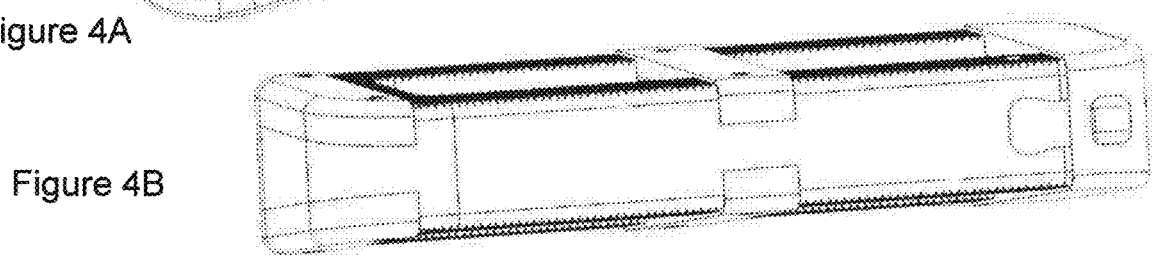
FIG. 4B shows the implant of FIG. 4A from a slightly different view.
Figure 4C:
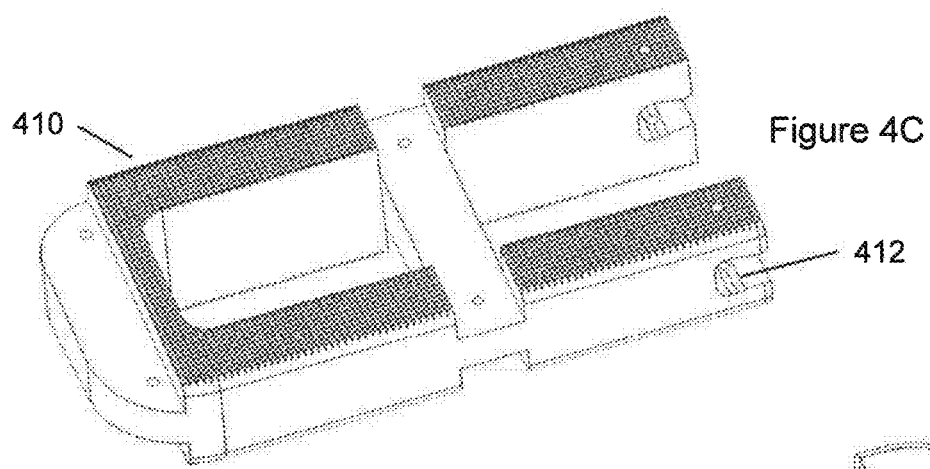
FIG. 4C shows the polymeric component of the implant of FIG. 4A.
Figure 4D:
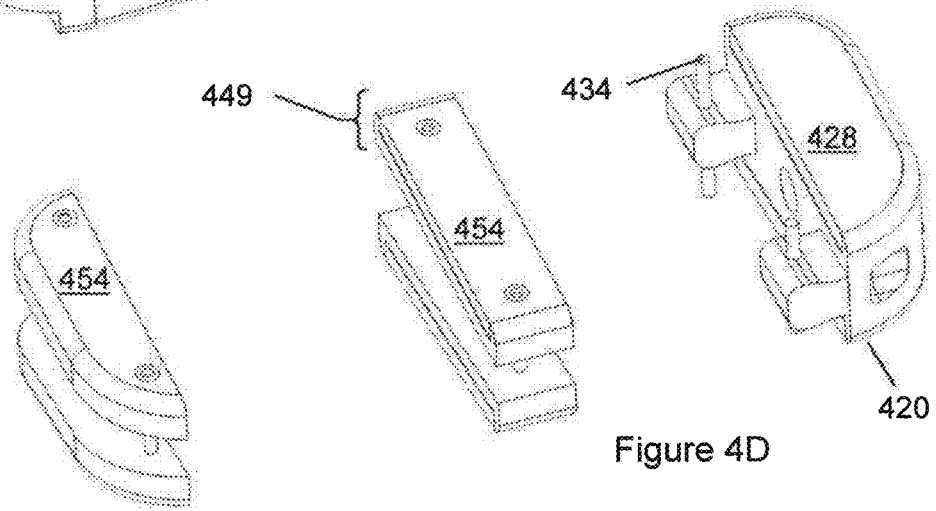
FIG. 4D shows the non-polymeric components of the implant of FIG. 4A.

Reference is now made to FIGS. 4A-4E, which illustrate an implant 400 intended for insertion via a lateral surgical approach. FIGS. 4A-4B show the assembled lateral implant 400. FIG. 4C shows the polymeric component 410 of the lateral implant 400. FIG. 4D shows the non-polymeric components of the lateral implant 400. By analogy with other embodiments described herein, lateral implant 400 can have central passageway 406A, 406B, polymeric component 410, recesses 412, trailing end component 420, recesses 422, central hole 424, substantially-solid region 426, porous region 428, protrusions 430, holes 432, pins 434, pins 444, solid regions 450 and 452, and porous region 454.

In plan view, such an implant 400 may have a wall that proceeds around the perimeter of the implant 400. Additionally, the implant 400 may have a ligament that connects a place on the wall with another opposed place on the wall. In combination, the wall and the ligament may define two openings 406A, 406B through the implant 400. In plan view, such an implant 400 may be elongated such that it has an aspect ratio (overall external dimension in one horizontal dimension divided by overall external dimension in a second horizontal direction orthogonal to the first horizontal direction) that is greater than 2:1, or greater than 3:1. If desired, for a highly elongated implant of this type, it would be possible to provide three openings through the implant instead of the illustrated two openings 406A, 406B.

The lateral implant 400 may comprise a polymeric component 410, which may comprise PEEK or PEEK enhanced with particles of an osseointegrative material. The implant 400 may also comprise one or more metallic components. The polymeric component 410 and the metallic component(s) may be arranged such that on the superior bone-facing surface of the implant 400, progressing around the circumference, there may be a sequence of polymeric surface, followed by metallic surface, and so on in an alternating progression. The same may be true for the inferior bone-facing surface. The metallic components may be mechanically joined to the polymeric component 410.

Some or all of the metallic components may comprise a region 450, 452 that is solid or substantially-solid, and may further comprise a porous region 454. The porous region 454 may be exposed to the exterior, i.e., may be bone-facing.

The implant 400 further may comprise an end component 430 that may comprise metal. The end component 430 may be solid or substantially solid, or it may have a substantially-solid region and a porous region. If a porous region 428 is present, it may have a bone-facing surface on the exterior of the implant 400. End component 420 may have protrusions 430 analogous to those in other implants. The implant 400 may be such that at the midplane, there is a continuous path of polymeric material except that the end component 430 of the implant 400 may be metallic.

For a lateral implant 400 as illustrated, a lordosis angle may be defined as the angle between a flat plane that is a generally flat surface that is tangent to or parallel to the top surface of the implant, and a generally flat surface that is tangent to or parallel to the bottom surface of the implant As illustrated, the lateral implant 400 exhibits some non-zero lordosis angle. This is visible in FIG. 4B. In FIG. 4B the difference in elevation between the metallic components and the adjacent polymeric component is also visible.

The lateral implant 400 as illustrated, has a longitudinal direction, between a first end and a second end. At a first end, which may be suitable to be grasped by an installation tool there may be a trailing end component 420. Trailing end component 420 may be all metal, although some region of it may be substantially-solid metal 426 and another region of it may be porous metal 428. The leading end, which is opposed to the trailing end, may comprise a superior bone-facing component comprising metal (which may comprise a substantially-solid region and a porous region), and an inferior bone-facing component comprising metal (which may comprise a substantially-solid region and a porous region), with the superior bone-facing component and the inferior bone-facing component joined to each other by pins 444.

Figure 4E:
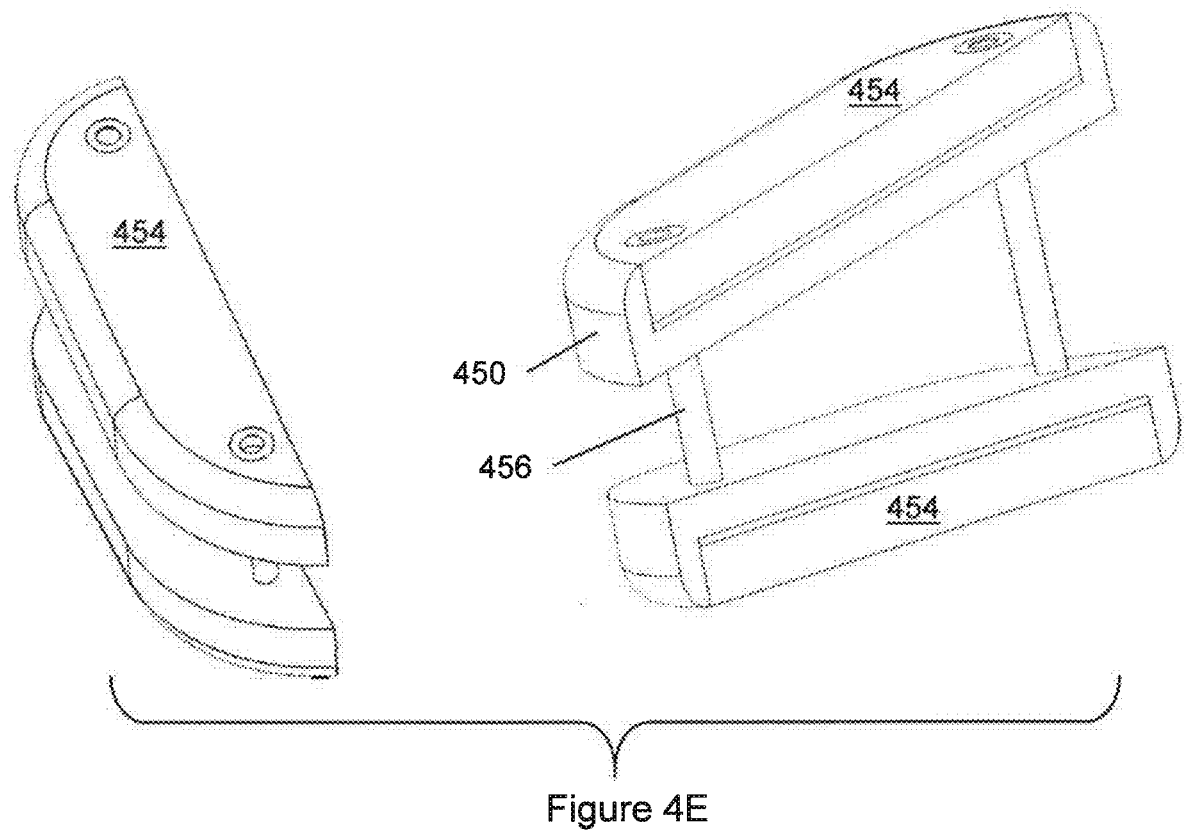
FIG. 4E shows views of metallic components at the distal end of the implant of FIG. 4A.
Figure 4F:
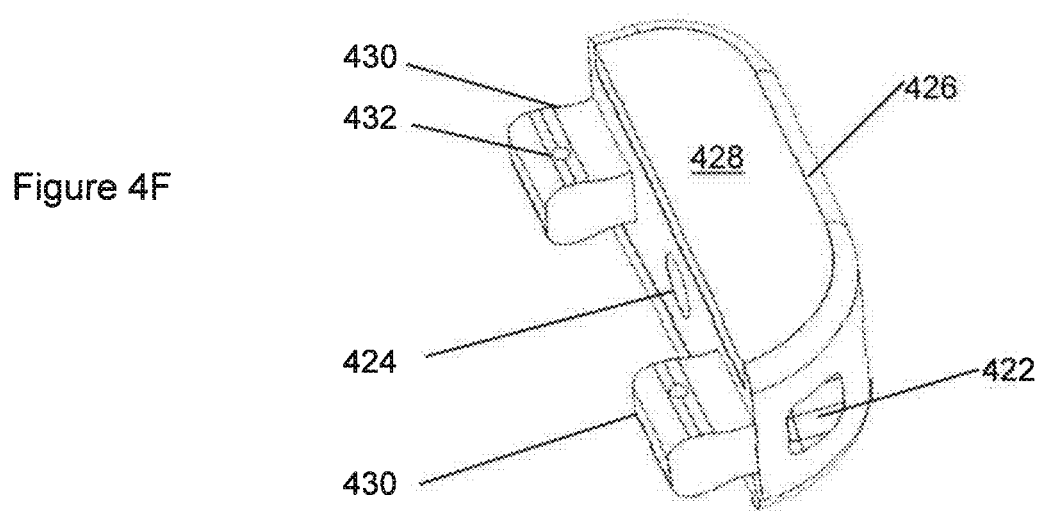
FIG. 4F shows views of metallic components located between the proximal end and the distal end of the implant of FIG. 4A

The lateral implant 400, as illustrated in FIG. 4E, has leading edge metallic components. These may form a barbell construct with each other, analogous to those described herein for other implants. Intermediate along the length of the implant 400 there also may be metallic pads 449 on the superior surface and the inferior surface of the implant 400, which may be on the ligament that spans between the two long sides of the implant 400. The pads 449 may be joined to each other by pins 456 in a barbell construct analogous to those described herein for other implants.

Cervical Implant

Figure 5A:
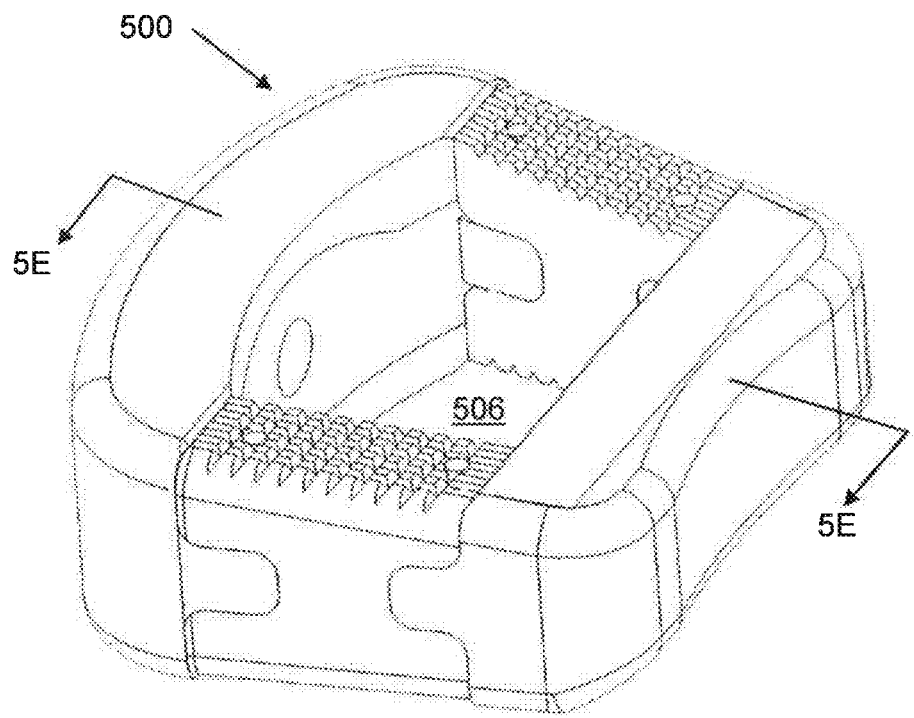
FIG. 5A is a three-dimensional view showing an implant suitable for use in the cervical spine. This may be termed a lordotic cervical implant.
Figure 5B:
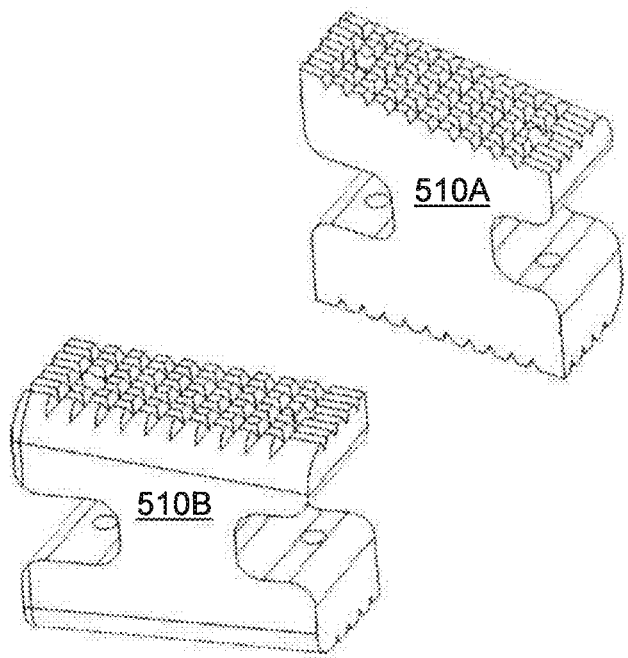
FIG. 5B shows the polymeric components of the implant of FIG. 5A.
Figure 5C:
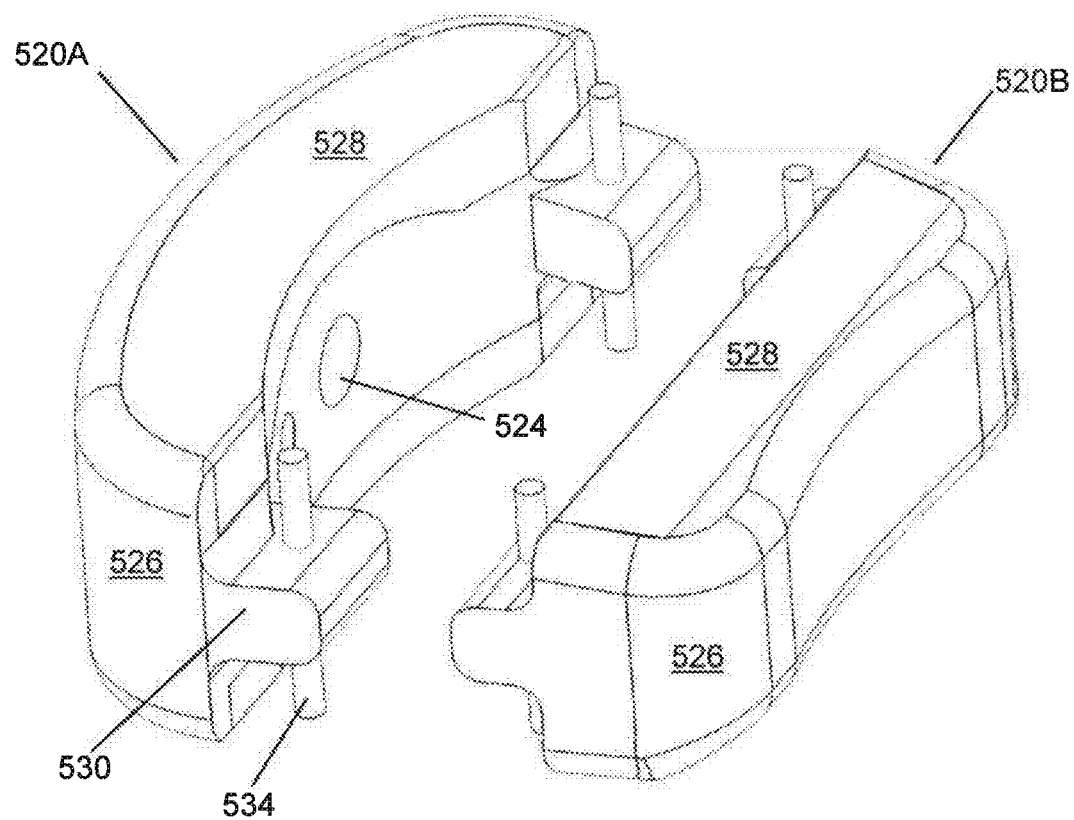
FIG. 5C shows the non-polymeric components of the implant of FIG. 5A.
Figure 5D:
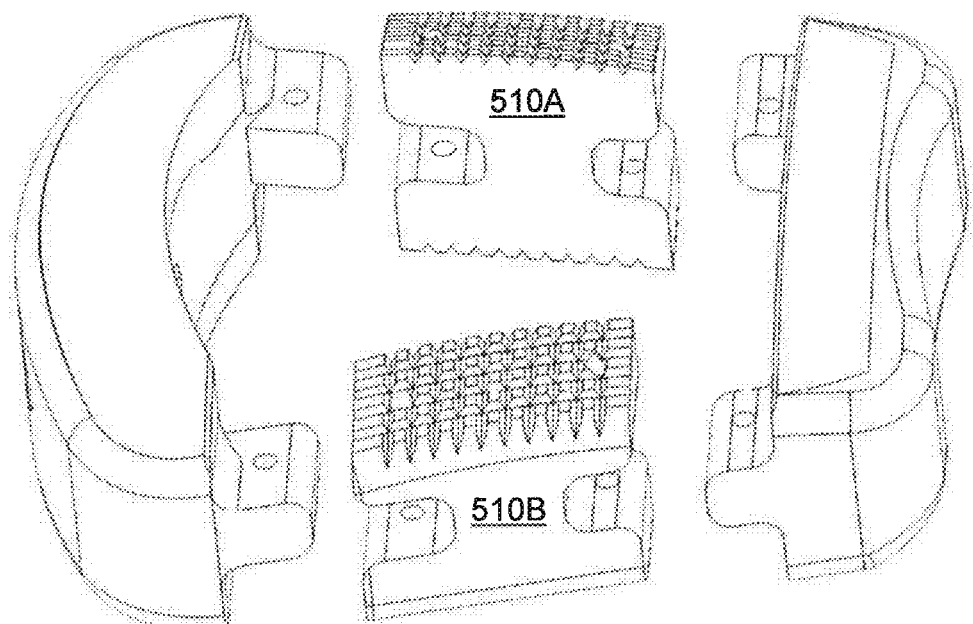
FIG. 5D shows an exploded view of the implant of FIG. 5A.
Figure 5E:
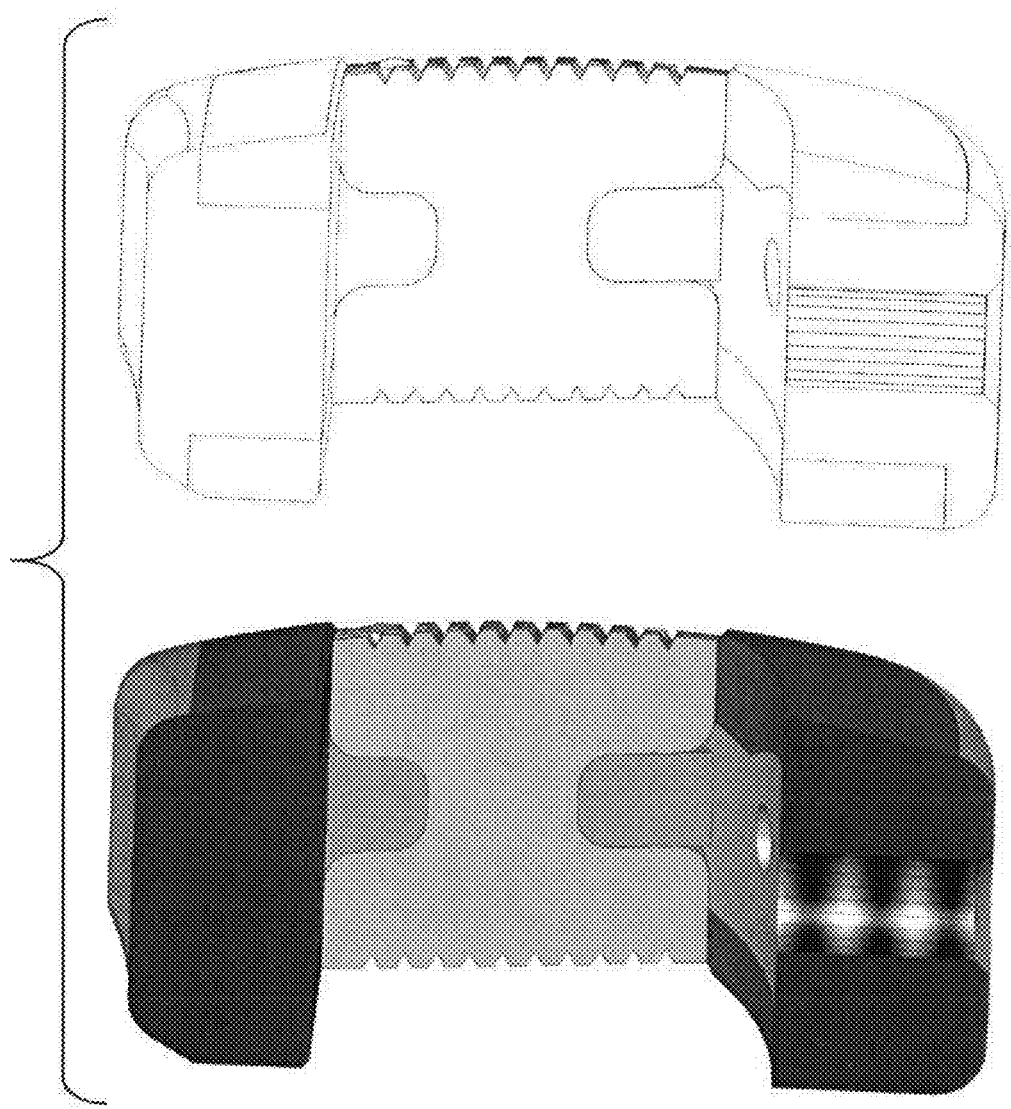
FIG. 5E shows a sectional view of the implant of FIG. 5A.

Referring now to FIG. 5A-5I, in an embodiment of the invention, there may be provided an implant 500 that may be suitable for use in fusion of the cervical spine. FIG. 5A shows an assembled cervical implant 400. FIG. 5B shows the polymeric component 510A, 510B of the cervical implant 400. FIG. 5C shows the non-polymeric components of the cervical implant 500. FIG. 5D shows the implant 400 exploded for ease of visualization. By analogy with other embodiments described herein, cervical implant 500 can have central opening 506, polymeric component 510A, 510B, trailing end component 520A, leading end component 520B, recesses 522, central hole 524, substantially-solid region 426, porous region 428, protrusions 530, holes 532, and pins 534. The implant 500 may have a first bone-facing surface and an opposed second bone-facing surface and a central opening 506 therethrough from the first bone-facing surface to the second bone-facing surface.

The implant 500 may comprise polymeric components 510A, 510B and metallic components 520A, 520B in the arrangement shown. As illustrated, in sequence from front to back of the implant 500, there may be a first metallic component 520A, followed by polymeric components 510A, 510B on respective sides, followed by a second metallic component 520B. Any of the metallic components may comprise a substantially-solid region 526 and a porous region 528. The porous region 528, if present, may be exposed on an external surface that is a bone-facing surface with respect to the position of the implant 500 when implanted in a patient.

As discussed elsewhere herein, the metallic components 520A, 520B may protrude further toward the bone than the polymeric components 510, while the polymeric components 510A, 520B may have a larger dimension of roughness than the metallic components 520A, 520B. This is visible in FIG. 5E.

Mechanical connection between respective components may be made by a pin 534 that may have a press-fit engagement with at least one of the components.

FIGS. 5A-5E show a cervical implant 500 such that both the upper surface and the lower surface are generally planar, in an overall sense (disregarding localized features such as peaks and roughness and the slight offset between the metal surface and the adjacent polymeric surface). A generally flat surface that is tangent to or parallel to the top surface of the implant, and a generally flat surface that is tangent to or parallel to the bottom surface of the implant, may form an angle with each other. The angle is a lordotic angle, and the implant may be termed a lordotic cervical implant.

Figure 5F:
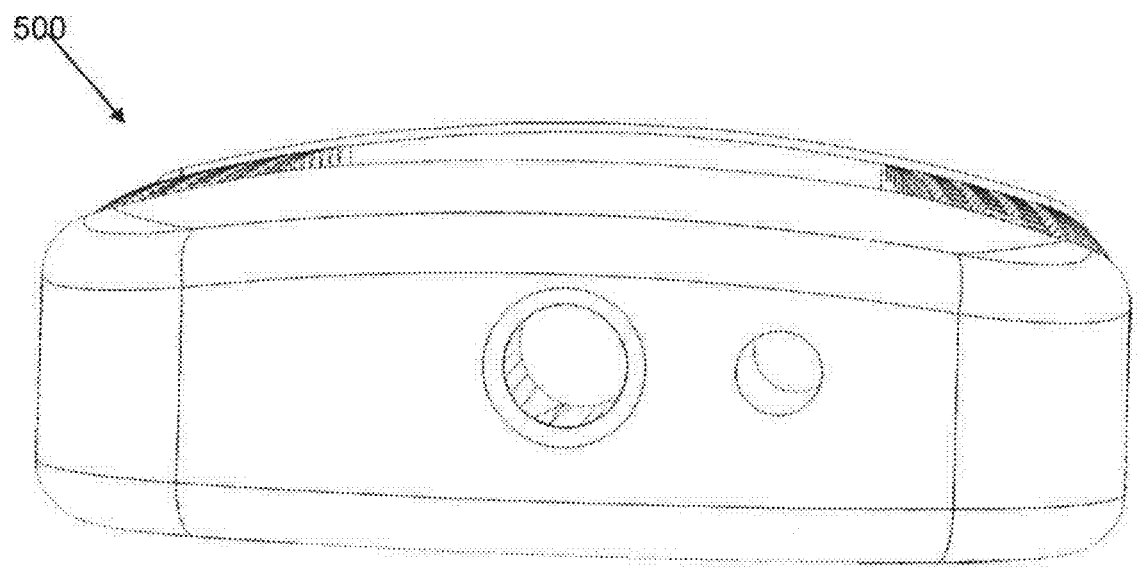
FIG. 5F is a three-dimensional nearly-frontal view showing another implant suitable for use in the cervical spine. This may be termed a convex cervical implant.
Figure 5G:
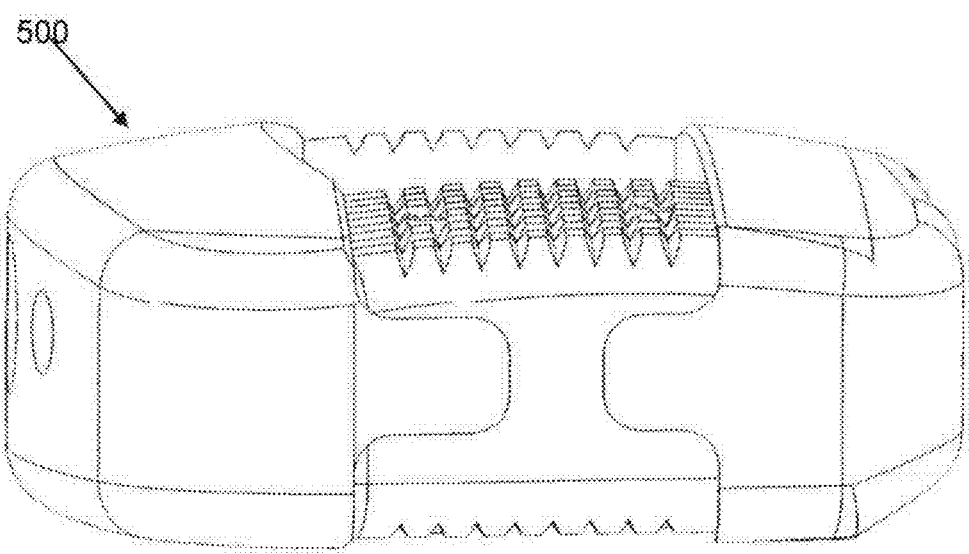
FIG. 5G is a three-dimensional nearly-side view of the implant of FIG. 5F.

FIGS. 5F-5G show a cervical implant 500 that may be referred to as a convex cervical implant. In this implant, just as in FIG. 5A-5E, the lower surface is generally planar, in an overall sense (disregarding localized features such as peaks and roughness and the slight offset between the metal surface and the adjacent polymeric surface). On the other hand, for the upper surface, an enveloping surface that would be locally tangent to the upper surface at a size scale larger than the roughness may have a compound curvature, such that it is curved in each of two directions that are orthogonal to each other. In FIGS. 5F-5G, the upper surface is convex in each of the two directions. Such an implant 500 may still have an overall effective lordosis, but such lordotic angle would have to be defined specifically in terms of where a defining plane is tangent to the compound-curved surface. As illustrated, the lordotic angle of the convex implant of FIGS. 5F-5G is approximately equal to the lordotic angle of the lordotic implant illustrated in FIGS. 5A-5E.

Figure 5H:
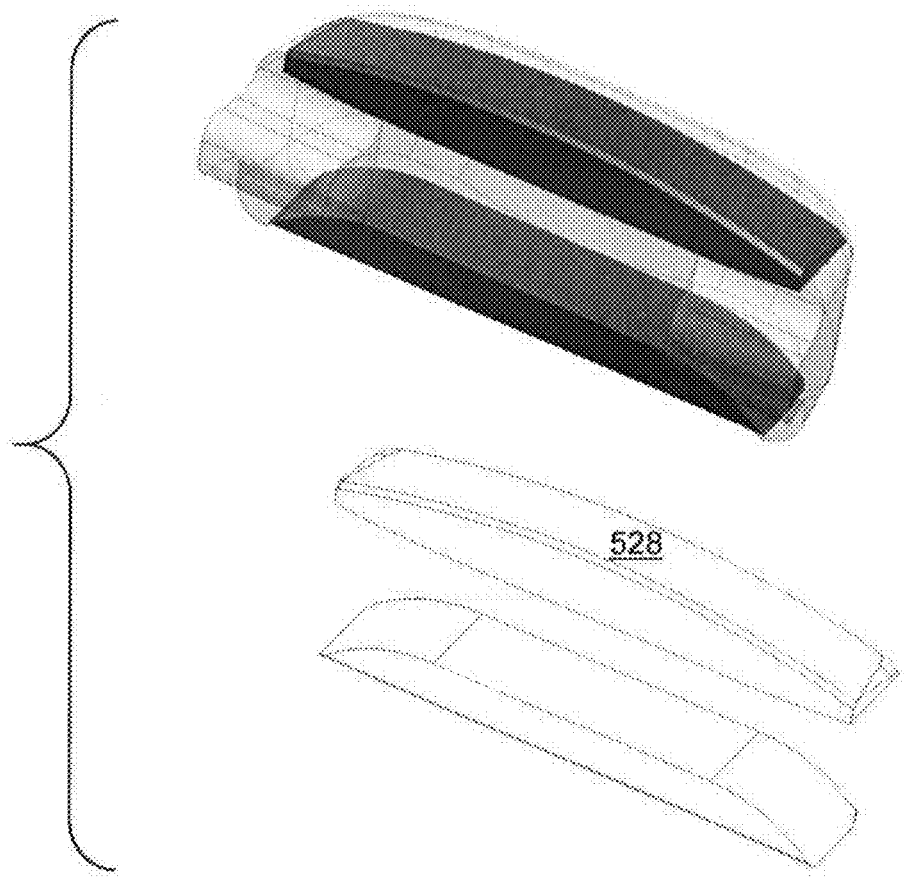
FIG. 5H shows a detail regarding the porous region in one of the cervical implants.
Figure 5I:
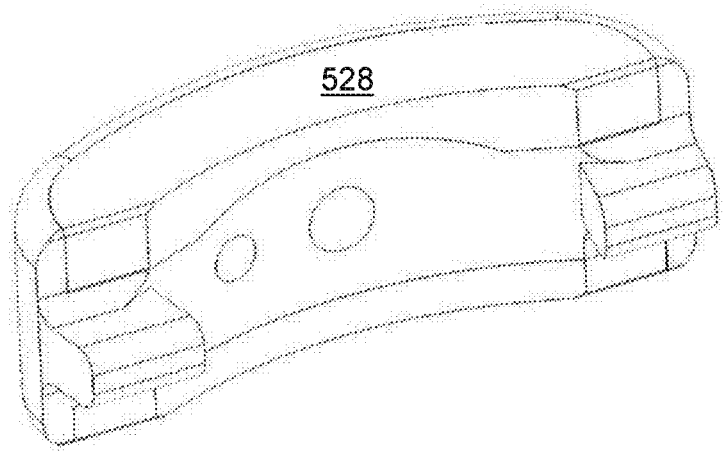
FIG. 5I shows another detail regarding the porous region in one of the cervical implants.
Figure 6A:
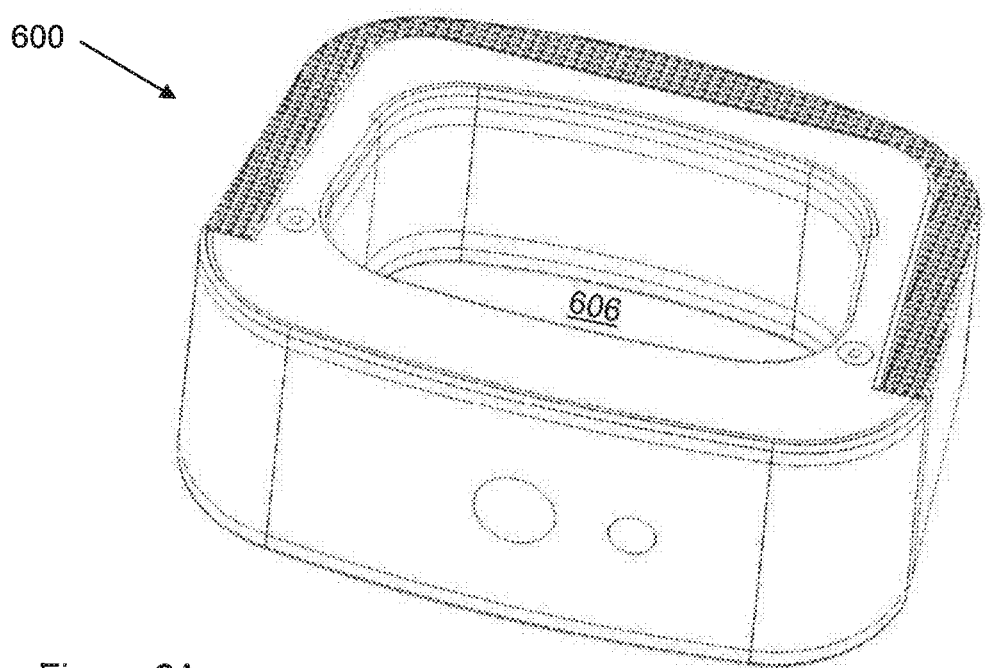
FIG. 6A is a three-dimensional view of an implant suitable for Anterior Lumbar Interbody Fusion.
Figure 6B:
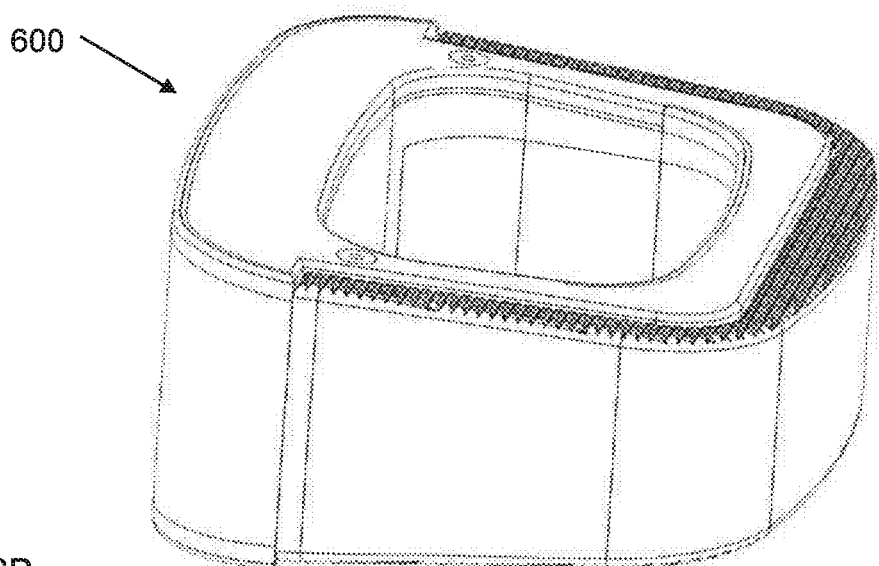
FIG. 6B is a three-dimensional view of the implant of FIG. 6A, from a different viewpoint.
Figure 6C:
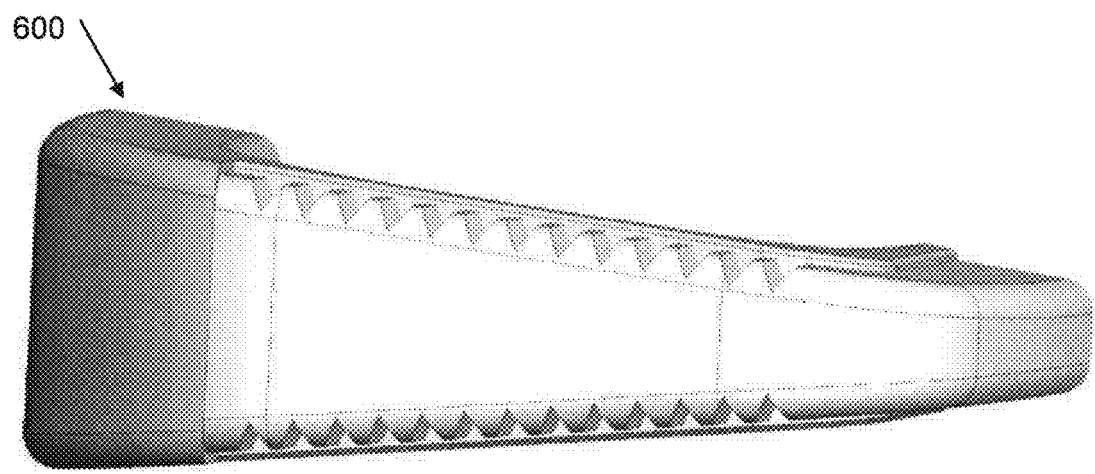
FIG. 6C is a side view of the implant of FIG. 6A.
Figure 6D:
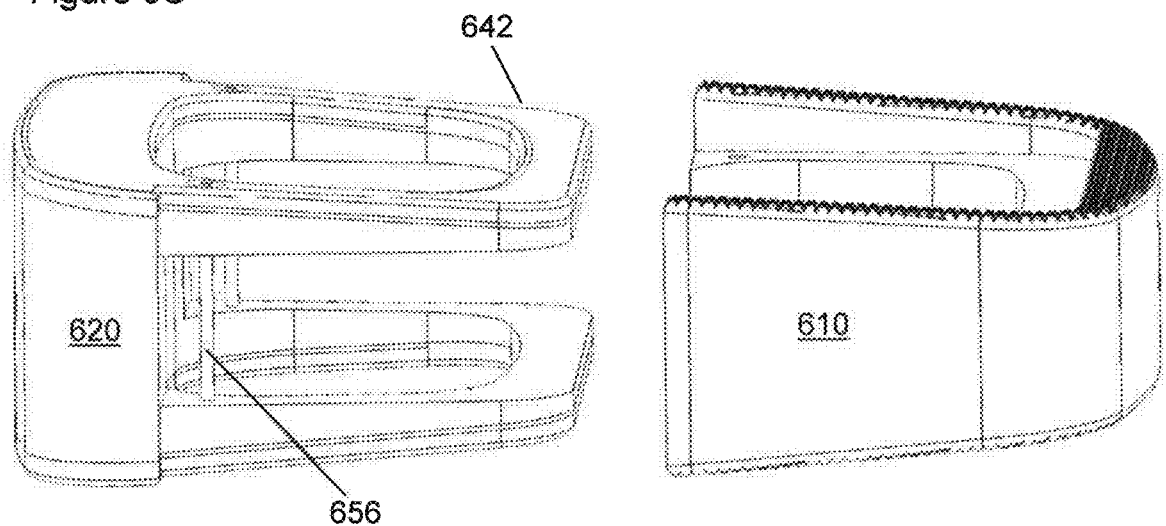
FIG. 6D is an exploded view of the implant of FIG. 6A.
Figure 6E:
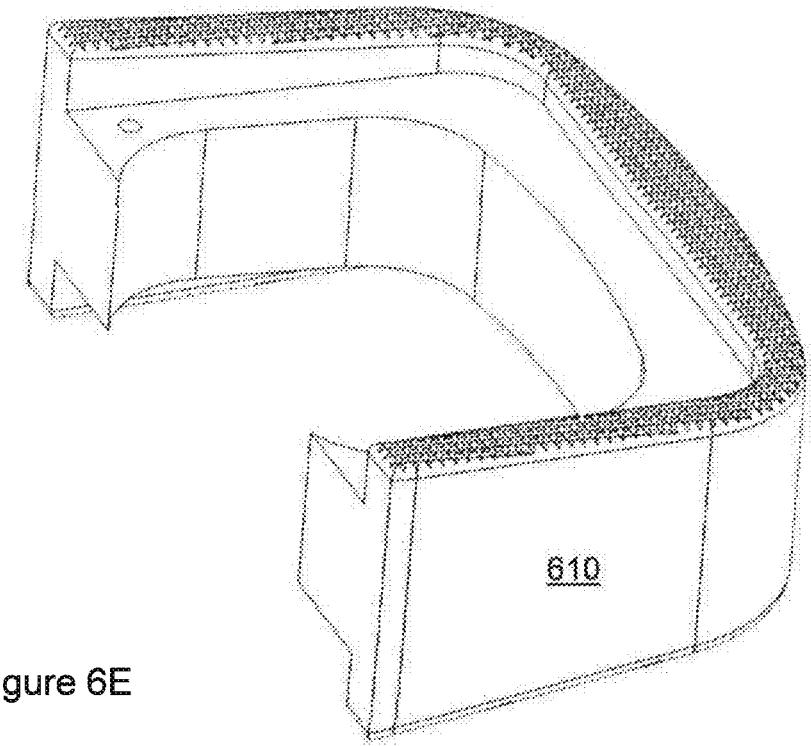
FIG. 6E shows the polymeric component of the implant of FIG. 6A.
Figure 6F:
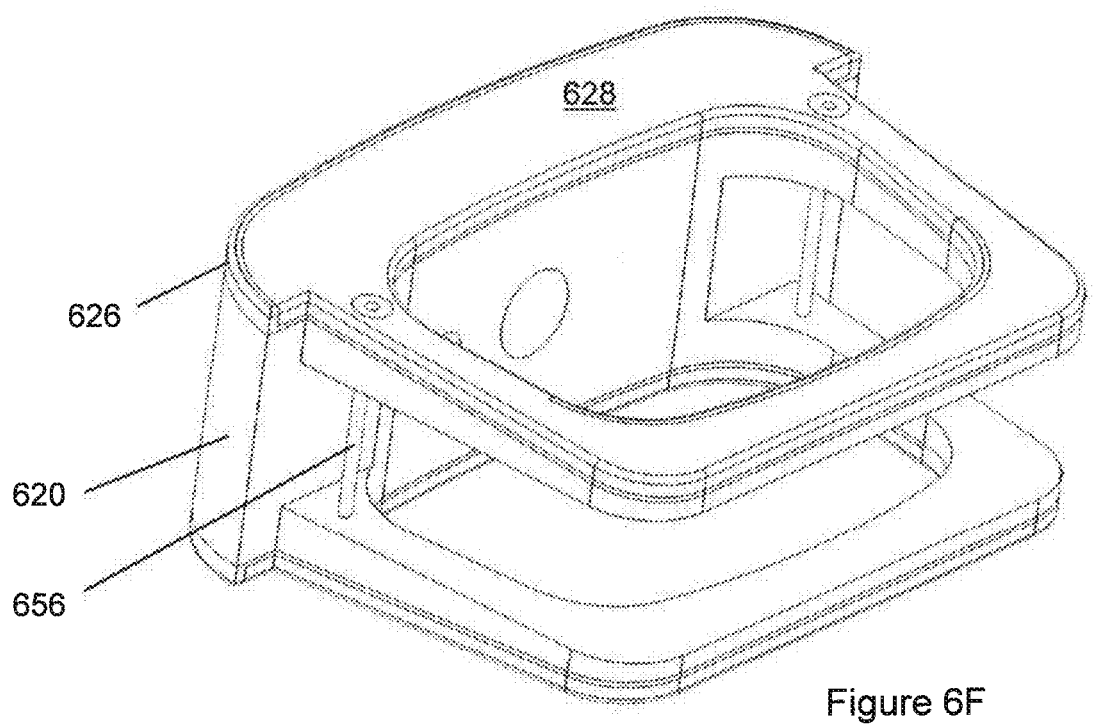
FIG. 6F shows the non-polymeric components of the implant of FIG. 6A.

Referring now to FIGS. 5H-5I, in regard to the porous region, the thickness (in the cephalad-caudal direction) of the porous region 528 does not have to be uniform across the extent of the metallic component in directions that are perpendicular to the cephalad-caudal direction, such as the lateral direction. Some examples of this occur in the cervical implant 500.

Referring now to FIG. 5H, the device may have a feature such that, in one of the metallic components, the porous region 528 has a thickness, measured in a direction that is perpendicular to a bone-facing surface of the porous region, such that the thickness is tapered in a direction from the first side polymeric component toward the second side polymeric component. At the posterior of the cervical implant 500, the porous region tapers toward each side of the implant 500, as a way of providing a gradual transition of properties and strength.

Referring now to FIG. 5I, the device may have a feature such that, in one of the metallic components, the porous region 528 has a thickness, measured in a direction that is perpendicular to a bone-facing surface of said porous region, wherein the thickness varies to accommodate a feature such as an instrument interface hole. At the anterior of the cervical implant 500, it is illustrated that the porous region is slightly thinner in the region of the instrument interface (draw-rod) hole, compared to its thickness in other places. This provides additional strength by in the vicinity of the draw-rod hole, by providing additional substantially-solid material in that vicinity.

ALIF Implant

Referring now to FIGS. 6A-6F, there is illustrated an implant 600 that could be used in an ALIF (Anterior Lumbar Interbody Fusion) procedure. The implant can comprise a polymeric component 610 and a metallic component 620 that are partially interleaved with each other. The metallic component 620 can have essentially a slot, into which a portion of the polymeric component 610 may fit. This may be thought of as a "hand-in-glove" configuration. The metallic component 620 and the polymeric component 610 can be interleaved such that at the anterior (trailing) edge the implant 600 is entirely metallic, and at the posterior (leading) edge the implant external surface is entirely polymeric, and at the interior of the central opening 606, the perimeter is entirely metallic at the superior surface and entirely metallic at the inferior surface but at the midplane the interior of the central opening 606 is a series of metallic and polymeric and metallic.

In an embodiment, there may be a ring 642 of metal going entirely around the perimeter of the device on the interior of the ring 642 at a first bone-facing surface, and there may be a ring 642 of metal going entirely around the perimeter of the tubular device on the interior of the ring 642 at a second bone-facing surface, and at the midplane there may be metal on only a portion of the interior of the ring 642. On the exterior of the ring 642, the exterior surface of the device may have exposed polymer on a majority of the exterior of the device.

In an embodiment, a majority of the sideways exterior side surfaces of the implant 600 may be polymeric, and on the interior of the central opening 606, there may be continuous metal all the way around the interior perimeter at one bone-facing surface and at a second opposed bone-facing surface but not at the midplane of the implant 600.

In an embodiment of the invention, the implant 600 may have a combination of components such that along the anterior-posterior direction, there is a series of materials in the order metal (anteriorly) followed by polymer followed by metal (posteriorly).

In an embodiment of the invention, the implant 600 may have a combination of components such that along the anterior-posterior direction, there is a series of materials in the order metal (anteriorly) followed by polymer followed by metal (posteriorly). The metallic component 620 can be subdivided into a substantially-solid region 626 and a porous region 628.

In the illustrated embodiment, the metallic surface may be more protruding toward bone than is the surface of polymeric component 610. The surface of polymeric component 610 may have engagement features 660 such as pyramids or sharp or pointed features such as to prevent expulsion of the implant 600. The engagement features 660 may have dimensions that are larger than the dimensions of any porosity or roughness that may be present on bone-facing surfaces of the metallic component 620, such as substantially-solid region 626 and a porous region 628. As illustrated, on the bone-facing surface, where metal is adjacent to polymer, the polymer is closer to the central opening or passageway 606 than is metal.

In the illustrated embodiment, the metallic component 620 may have some substantially-solid region 626, and some porous region 628. The metallic component 620 and the polymeric component 610 may be joined to each other by a pin 644 in a press-fit condition. In such a situation, for compression in the cephalad-caudal direction, the overall modulus of much of the implant may be similar to the modulus of natural bone, because the modulus of PEEK more closely resembles the modulus of natural bone than does the modulus of solid titanium.

In ALIF implant 600, it is provided that in metallic component 620, the porous region 628 extends to the edge of metallic component 620 where the metallic component 620 borders on central opening 606. It is believed that this feature provides encouragement for bone at the contacting vertebra endplate surface, to enter the porous region 628, and to continue to grow into the interior region or central opening 606 of implant 600. In spinal fusion surgery, it is typical to place bone chips and growth-promoting substances of various sorts in central opening 606 to encourage bone to grow in and form a continuous bony structure from one vertebra to the next vertebra. In somewhat more detail, it is illustrated that, of the four sides of the implant 600, facing central opening 606, this porous edge occurs on three sides (the anterior and two lateral sides). On the other hand, the edge at the posterior is illustrated as being substantially solid metal, which provides additional strength at that location.

As illustrated, implant 600 also has a pin 656 that may be press-fitted into metallic component 620 at both or at least one of its ends. The pin 656 may anchor polymeric component 610 in assembly with metallic component 620.

Further Details about Press Fits

Mechanical fits are described in references such as ANSI B4.1 standard, in regard to dimensions of parts and also tolerances on those dimensions. A pin or shaft or cylindrical object may be described, including its tolerance, so as to have a maximum permissible outside diameter and a minimum permissible outside diameter. Similarly, a hole may be described as having a maximum permissible inside diameter and a minimum permissible inside diameter. A slip fit is when any combination of permissible inside diameter and permissible outside diameter has a gap between the hole and the cylindrical object. An interference fit is when any combination of permissible inside diameter and permissible outside diameter has interference between the hole and the cylindrical object. A transition regime is when some combinations of permissible inside diameter and permissible outside diameter have a slip fit while other combinations of permissible inside diameter and permissible outside diameter have an interference fit. In embodiments of the invention, dimensions and tolerances may be chosen to result in an appropriate amount of interference such that at the loosest condition there is an interference fit sufficient to keep the parts together as desired, and the tightest condition, which is also an interference fit, the fit is still easy enough to assemble. For example, it is believed that for nominal diameter of 0.031 inch, and what may be described as a light drive fit (F1), appropriate dimensions for the pin may be 0.0315/0.0313 inch, and appropriate dimensions for the hole may be 0.03125/0.03100 inch. This results in an interference that can range from 0.0005 inch to 0.00005 inch depending on the combination of permitted diametral dimensions. However, it is not wished to be limited to these dimensions. It would also be possible to use a medium drive fit (F2) or other fit as desired. Furthermore, for example, when one of the components of the interference fit has a modulus of elasticity that is different from the modulus of elasticity of the other component, some adjustment to such ranges of dimensions may be appropriate.

When two components are mechanically joined to each other, such mechanical joint can be a pinned joint in which a pin such as a cylindrical pin extends through both components and is interference-fitted or press-fitted into at least one of the components. As illustrated, such pins may be oriented in a generally caudal-cephalad direction, although other directions are also possible.

A press-fit condition can be achieved, as in known machine shop practice, by providing a known, small amount of dimensional interference between parts that are intended to mate with each other, such as a dowel pin and a hole. Because of close tolerances required on both the pin and the hole, the dowel pin is typically finish-manufactured by a grinding operation and the hole is typically finished by a reaming operation. For diameters of current interest, which are in the range of 1 mm, the interference (overlap in diameters of the pin and the hole when each of those components is measured in a separated condition) is described herein. A press-fit is often used with parts that are metal. In situations of interest to the current application, it may be desirable that the pin be made of metal and, where a hole for press-fit is provided, that hole be provided in metal that is substantially solid (rather than the porous region described herein). The press-fit would most commonly be a cylindrical pin engaging with a cylindrical hole, although other shapes and geometries are also possible.

In a situation in which a press-fit pin passes successively through three different components or regions or materials along the length of the pin, it is possible that a press-fit condition could exist in all three places. However, it is also possible that the assembly could hold together satisfactorily if a press-fit condition exists at less than all three places. For example, it might be sufficient if a press-fit condition only exists at two out of the three places, such as a press-fit existing at one end of the press-fit pin and at the other end of the press-fit pin, while a somewhat looser condition might exist around the middle of the press-fit pin. This situation can occur in FIG. 1F. For some designs involving three regions of contact with one pin, it would be possible that only one of the regions of contact might be a press-fit, and the assembly would still hold together. This situation can occur in FIGS. 3C, 4D. It is possible that the pin could have a press-fit relationship with the hole in the body, or, alternatively, the pin could have a relationship with the hole in the body that is less tight than a press-fit. In the TLIF design illustrated herein, there is a press-fit pin passing through three layers of materials that could be adequately constrained by press-fitting in only one of the three layers of materials, i.e., the central layer. It is also possible that the fit between some of the components could be a tight press-fit and the fit between other components could be a lighter press-fit or a sliding fit. All of this can be accomplished by appropriate dimensions and tolerancing. In general, any combination of tightness of press-fit or looser form of fit may be provided.

In situations where a pin exists in two different materials, it is possible that press-fit in only one of those two materials is sufficient. For example, in the PLIF design illustrated herein, where the end component joins to the polymeric component in two distinct places one upper and the other lower, it is sufficient if press-fit condition exists only one of the two places, such as at the pin-to-metal interface.

In the "barbell" designs illustrated herein, the holes in both metallic components could be through-holes, or the hole in one of the metallic components could be a blind hole while the hole in the other of the metallic components could be a through-hole, or it is even possible that the holes in both metallic components could be blind holes. To create the press-fit, the pin may have dimensional interference with the corresponding hole in each of the metallic components.

In a metallic component that receives a press-fit pin and contains both a porous region and a solid region, if the press-fit hole goes through the bone-facing surface, there may be provided a region of the bone-facing surface that is solid or substantially-solid in the vicinity of the press-fit. Alternatively, if the hole for the press-fit with the pin is a blind hole, the entire bone-facing surface of the metallic component, or the bone-facing surface that is in line with the pin, may be porous. In such a situation, away from the bone-facing surface there may be provided a solid or substantially-solid region in which the press-fit occurs. As yet another alternative, it would be possible to provide a press-fit hole that extends through both the substantially-solid region and the porous region. In such a situation the press-fit with the pin in the porous region might not be as tight as the press-fit with the pin in the substantially-solid region, but still there would be a press-fit in some places to accomplish the desired assembly.

It is illustrated that the exterior-facing surface of pad 149 comprises some porous metal, and also comprises substantially-solid metal that surrounds the pin 156 and participates in a press-fit. It is also illustrated that the interior-facing surface of a pad such as pad 149 comprises entirely substantially-solid metal. It is also possible that the interior-facing surface of pad such as pad 149 may comprise less than all but still a majority of substantially solid metal without actually being entirely substantially-solid metal. As illustrated, the exterior-facing surface of pad such as pad 149 may have a majority of porous metal and a minority of its surface represented by the exposed substantially-solid metal together with the pin.

In various places in implant 100, different press-fit geometries exist. Some of the press-fits are "barbell" constructs, and so in order for the implant to remain assembled, it is necessary for all of the metal-to-metal press-fits to remain tight. With a "barbell," it is less important what kind of fit there is between the pin and the polymeric component, as long as the pin is not allowed to buckle during press-fitting. In fact, for that situation, less friction between the pin and polymeric component might be preferable because if there is an upper practical limit to the amount of insertion force that can be applied to the pin, such a distribution of fits and tolerances would allow a larger proportion of that insertion force to be used for creating the final metal-to-metal press-fit during assembly. In contrast to this situation, there is also another type of situation that involves capturing of one part in another part. In some situations, in addition to press-fitting of a pin, there is also a geometric capturing relationship where the metal end piece joins the PEEK body, and so even if one of the fits (the fit of the pin in the polymeric component or the fit of the pin in the metal) is loose, the other press-fit will keep the implant together successfully. In such a situation it would be possible to have the pin/polymer fit being loose and pin/metal fit being tight, or to have the pin/polymer fit being tight and the pin/metal fit being loose. (Of course, it is also possible that both fits could be tight). A capturing relationship could exist where an overall feature of the metallic component slides into a corresponding feature of the polymeric component or vice versa. Such a relationship could constrain relative motion between the two components in some directions but allow motion along the direction of insertion for coupling the two components. Then, a press-fit pin could further constrain and couple the two components.

It would also be possible, if desired, to provide some form of supplemental fixation in addition to the described press-fit involving the pin. For example, after assembly, a pin could be spot-welded to its neighboring metallic component. It would also be possible to plastically deform a localized region of the pin or of one of the metallic components that is in contact with the pin. It is possible that when a pin is shortened after press-fitting, that cutting operation could be performed in such a way as to leave a burr or similar feature that contributes to locking. It would also be possible that one of the metallic components has a metallic component polymer-facing side surface, and the polymeric component has a corresponding polymeric component metal-facing side surface, and there could be an interference fit between the metallic component polymer-facing external side surface and the polymeric component metal-facing side surface.

Method of Assembly

Embodiments of the invention may comprise a method of assembly.

It can be noted that, especially in configurations such as the "barbell" configuration, the pin involved in press-fit may be somewhat long and slender. If compressive force needs to be applied to the pin to force the pin into press-fit engagement with a metallic component, and if the force is applied at the pin end opposite from the press-fit, and if the pin were unconstrained over much of its length, it is possible that the pin could be vulnerable to buckling. Therefore, a possible assembly sequence is described here. Initially, the pin and one metallic component such as pad 149 could be urged into press-fit engagement with each other, in isolation from any other components of the implant. This engagement process could be performed with the pin being held in a chuck or similar tooling that grasps much of the length of the pin, or with the pin being provided with some form of close but slightly loose sideways constraint or support such as a close-fitting but slightly loose hole. Such support or constraint could prevent buckling of the pin during this step of the assembly. Then, the pin (such as 156, 256, 356, 456) can be inserted into the hole in the polymeric member (110, 210, 310, 410, 510). The hole in the polymeric member can be sufficiently loose with respect to the pin that there is no risk of causing the pin to buckle as the pin is inserted into the hole. Finally, the pin can be urged into engagement with the second metallic component by application of opposed compressive forces to the two metallic components. While this application of force is occurring, the hole in the polymeric member can provide sideways support to the pin to prevent the pin from buckling during application of insertion force. The polymeric member and the pin could have a sliding fit with respect to each other, or could be a transitional fit (which might be either sliding or interference depending on the stack-up of tolerances in an individual situation), or the fit in the polymeric component could be a press-fit but looser than the press-fit in the metallic component). Alternatively, the pin could first be inserted into the hole in the polymeric part, and then the two pads could be press-fitted onto respective ends of the pin. Other assembly sequences are also possible.

This principle can also be used in other situations. For example, in the TLIF implant 300, a pin (such as 334) may pass through a polymeric component 310 and a metallic component and polymeric component 310. The pin 334 may be inserted first through the polymeric component 310, which may have a looser-than-press-fit relationship with the pin, and then may be forced through the metallic component in a press-fit relationship. During this step, the extending part of the pin 334 may be grasped in a held in a chuck or similar tooling that grasps much of the length of the pin and urges the pin into its press-fit. The chuck can be repositioned as needed. During this process, the hole in the polymeric piece 310 can provide support to prevent the pin from buckling. Then, the pin 334 can be urged further in so that the pin 334 extends beyond the metallic component into the polymeric component 310, where the fit can again be looser than a press fit. If the fit between the pin 334 and the polymeric component is slightly looser than a press fit, that can reduce unnecessary exertion of force onto the pin 334 while still allowing the necessary exertion of force for achieving press-fit where needed.

It is possible that at the time of installing the pin (such as 156, 256, 356, 456, 656) and making the press-fit, the pin may be longer than the eventual pin in the completed implant (100, 200, 300, 400, 500, 600). Such extra length of the pin may, for example, be useful for the grasping of the pin by a chuck or other tooling used during certain steps of the assembly process. The excess length of the pin may be removed at an appropriate time in the later part of the assembly process, such as by a machining operation or other operation.

Yet another possibility is that a pin can be press-fitted into a blind hole (in contrast to a through-hole) in a metallic component.

Manufacturing Sequence

Described here is a possible manufacturing sequence for embodiments of the invention. It can be understood that described steps can be omitted or changed or re-sequenced if appropriate for a particular situation. Polymeric components can be manufactured by molding or machining or a combination thereof. In regard to metallic components, a first step can be to manufacture, by additive manufacturing techniques, an early-stage metallic component. For metallic components, the process may start with a powder of metal particles, such as particles of titanium or a titanium alloy. The particles may be joined to each other or merged with each other by application of energy such as by laser melting or laser sintering or by electron beam. It might also be possible, in selected applications, to use a three-dimensional printing process involving a binder fluid applied to the powder bed in selected places. The manufacturing process may be controlled by software instructions that may be unique to a particular design. Such early-stage part can contain both substantially-solid regions and porous regions, as may be dictated by the design of the part and as may be controlled by software instructions governing the manufacturing process.

After the early-stage part is retrieved from the additive manufacturing process, machining operations can be performed if desired. Such machining may be performed primarily or entirely on portions of the early-stage part that are substantially solid. Features that are holes in the finished product do not need to be manufactured as holes in the early-stage part. For such features, the early-stage part can be substantially solid in the relevant region and holes can be drilled in the substantially solid material during the machining process. This includes holes intended to be occupied by pins for press-fits. For such holes, the early-stage part can be additively manufactured as substantially-solid material in the appropriate place, and afterward a hole can be drilled through the substantially-solid material, and after that drilling, the drilled hole can be reamed to achieve the final hole dimension with required accuracy. There may be other holes, not involved in press-fits, that may be drilled in substantially-solid material without being reamed afterward. There may be holes that are intended to be internally threaded, such as for interface with a draw-rod. For such holes, the early-stage part can be additively manufactured as substantially-solid material in the appropriate place, and afterward a hole can be drilled through the substantially-solid material, and after that the drilled hole can be tapped to create the internal threads.

When working with the early stage part, it is also possible to use machining operations to create certain surfaces, such as flat surfaces, on the part. For example, there may be flat surfaces that are involved in the interface of the metal component with the polymeric component. This may occur at protrusions from the metal component that interact with corresponding features of the polymeric component. Protrusions such as protrusions 130, 230, 330 can be machined on their side surfaces. Such side surfaces, which may interact with corresponding machined surfaces of polymeric part 110, 210, 310, can be involved in the trapping or other spatial relationship described elsewhere herein. The dimensions and surface condition of machined surfaces can be more precisely controlled than the dimensions and surface condition of surfaces as they result from the additive manufacturing process. Flat surfaces on the substantially-solid portions of pads 149 could be machined if desired although they do not have to be. Exterior-facing surfaces of metallic components do not have to be machined.

After machining, a part can be anodized if desired, such as to provide desired surface treatment or properties or to provide desired colors.

After that, the implant can be assembled, such as to join metal components together with the polymeric component. This can include performing press-fits as appropriate.

After that, the assembled implant can be sterilized with, if necessary, the implant being enclosed in a pouch. Any of various appropriate sterilization procedures can be used, as known in the industry. If sterilization by heat is used, it may be appropriate to eliminate the possibility of liquid water entering and remaining in crevices or pores of the implant. For example, dry heat sterilization can be used. If steam sterilization is used, it is possible to use cycles that include extended drying time at temperature, to ensure the evaporation of all liquid water.

For a surgical procedure, it is possible to provide a variety of sizes of implants, which may also include a variety of lordosis angles in combination with a variety of sizes of implants. Appropriate installation instruments can also be provided.

Anatomy

FIGS. 7A-7E illustrate various of the described implants in relation to vertebrae near which they would be implanted.

In the illustrated vertebrae, in the body of the vertebra that normally adjoins the spinal disc (not illustrated), the body of the vertebra has an internal structure, similar to other bones. In general, the outer or more external region of a vertebral body contains relatively stronger and denser bone. The outer, harder denser bone is referred to as the apophyseal ring. In contrast, the interior region of a vertebral body contains bone that is less dense and softer and weaker. In some vertebrae such as the cervical spine, on the surface or endplate of the vertebral body facing the spinal disc or the implant, there is a concave surface of the bone.

Figure 7A:
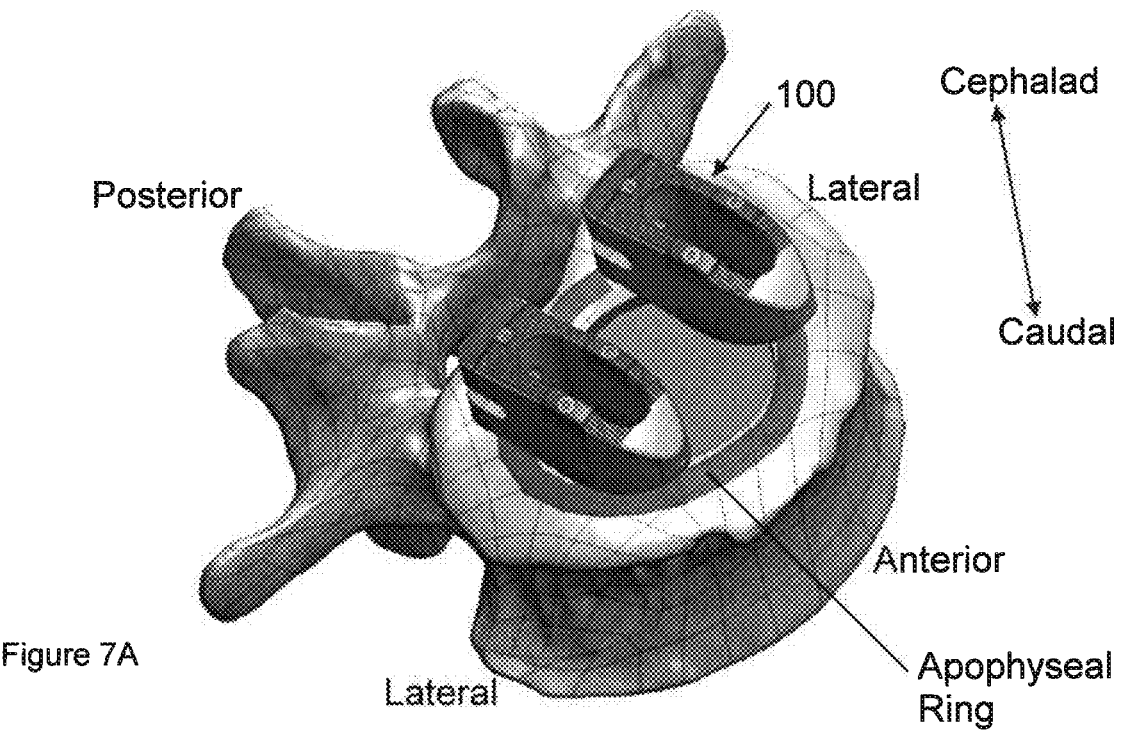
FIG. 7A shows a PLIF implant in relation to a vertebra.

Referring now to FIG. 7A, implant 100 may be implanted as a pair of implants 100 in a spinal disc space. FIG. 7A illustrates a pair of PLIF implants 100 in relation to a lumbar vertebra near which they may be implanted. As illustrated, the outwardly-located (laterally-located) metal components located in the most extreme anatomically lateral locations are in contact with the apophyseal ring, thereby achieving strong bony fixation with the strongest bone of the vertebral endplate. As illustrated, the metal components located more anatomically medially are in contact with the concavity of the vertebra thereby improving friction between the implant and bone. The metallic components achieve contact with the vertebrae at the time of implantation. The polymeric components 110 may achieve contact with the vertebrae upon settling (subsidence) or application of compressive load along the spine.

Figure 7B:
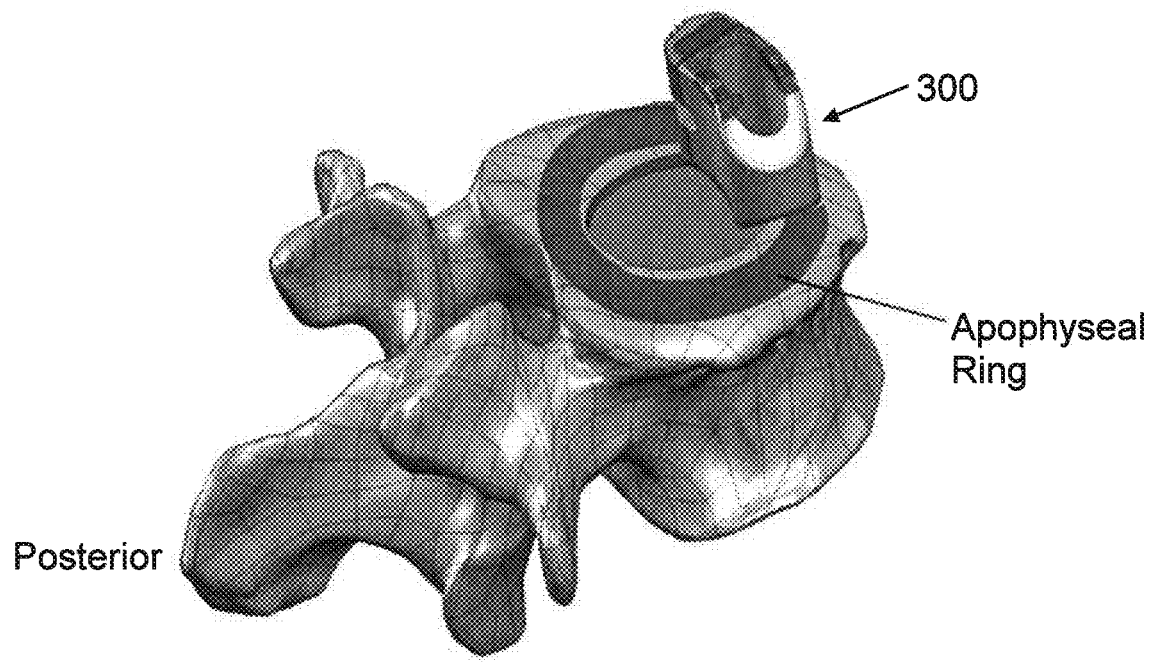
FIG. 7B shows a TLIF implant in relation to a vertebra.

Referring now to FIG. 7B, there is illustrated a TLIF implant 300 in relation to a lumbar vertebra near which it may be implanted. With the TLIF implant 300, one of the long curved sides of the implant 300 (the side that is placed more anteriorly) is in contact with the apophyseal ring. That long curved side comprises some polymeric surface and some metal surface. The other long curved side of the implant 300 (which also comprises some polymeric surface and some metal surface), is in contact with less-dense bone. The more anteriorly (anatomical direction) located metal component, which is in contact with the apophyseal ring, may achieve strong bony fixation. The more posteriorly (anatomical direction) located metal component may be in contact with the concavity of the vertebral endplate, thereby achieving good friction. The polymeric component 310 achieves contact with the vertebrae upon settling or application of compressive load along the spine.

Figure 7C:
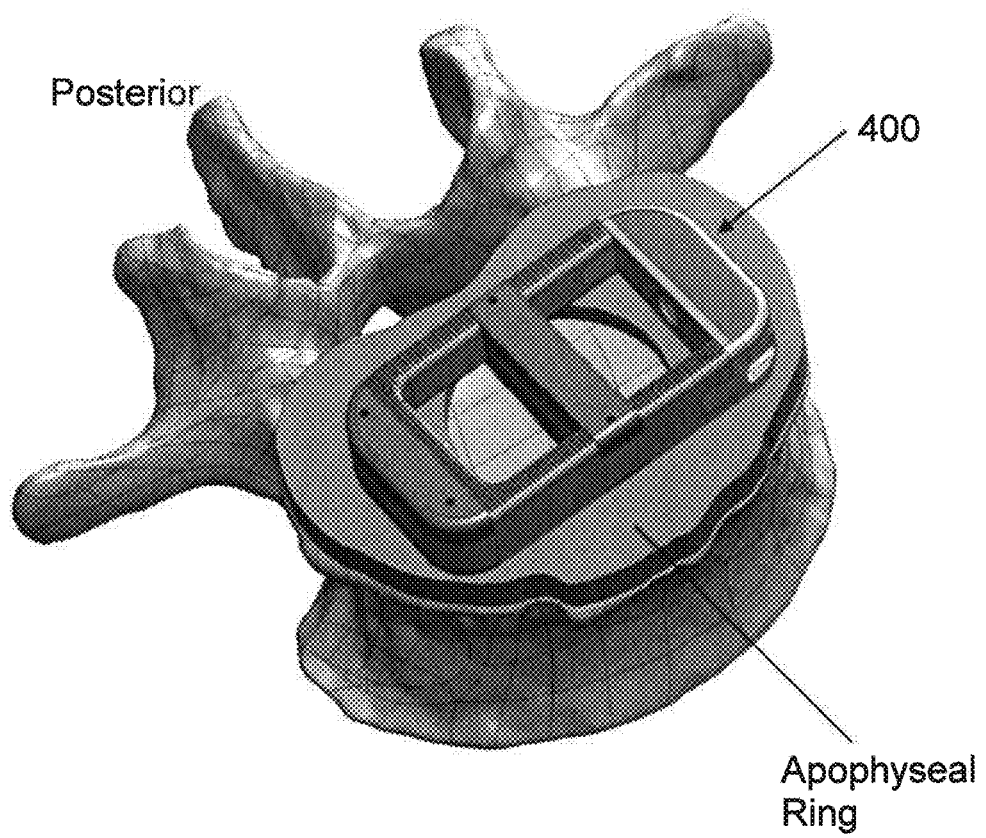
FIG. 7C shows a lateral implant in relation to a vertebra.

Referring now to FIG. 7C, in regard to lateral implant 400, the lateral sides of the implant 400, which have metal surfaces of end component 420 and pad 449 at an end of implant 400 that is opposite end component 420, are in contact with bone of the apophyseal ring. FIG. 7C illustrates a lateral implant 400 in relation to a lumbar vertebra near which it may be implanted. Sets of metallic components 420 at the instrument-interface trailing end component 420 contact the apophyseal ring. Sets of metallic components such as pads 149 at the leading end opposite the end component 420 also contact the apophyseal ring. A set of metallic components 450 in the middle of the lateral implant 400 may contact the center on the concavity in the vertebral plate, which may maximize bony contact/friction.

Figure 7D:
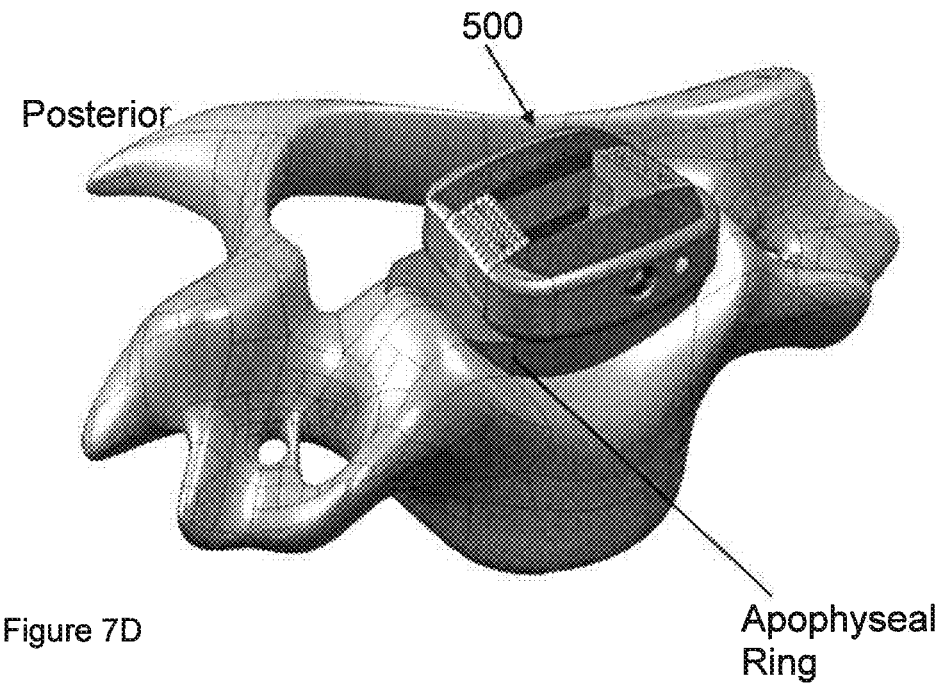
FIG. 7D shows a cervical implant in relation to a vertebra.

Referring now to FIG. 7D, FIG. 7D illustrates a cervical implant 500 in relation to a cervical vertebra near which it may be implanted. The bone-facing surface of the implant 600 may generally be in contact with the apophyseal ring of the vertebral body.

Figure 7E:
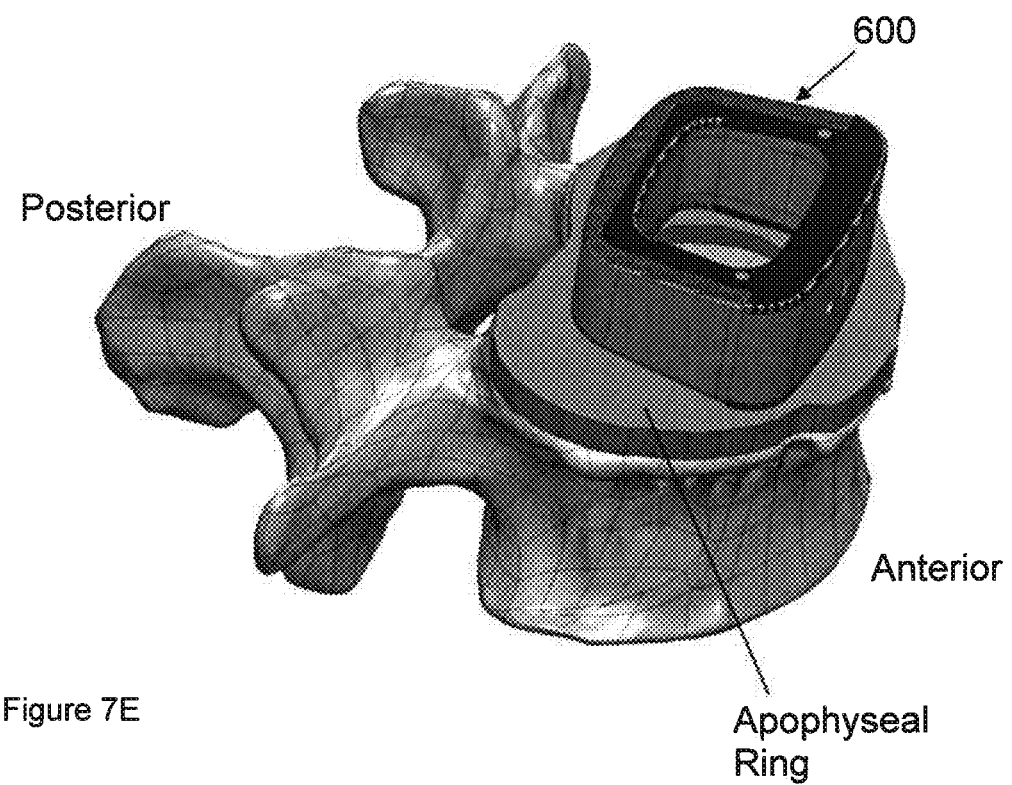
FIG. 7E shows an ALIF implant in relation to a vertebra.

FIG. 7E illustrates an ALIF implant 600 in relation to a lumbar vertebra near which it may be implanted. The perimeter of the ALIF implant 600 may roughly correspond to the apophyseal ring. The bone-facing surface of the implant 600 may generally be in contact with the apophyseal ring, while the concavity of the vertebral plate may be in contact with bone graft material in the central opening 606.

With spinal implants in general, it can be desirable that portions of the implant be radiolucent as a way of allowing long-term monitoring of bone ingrowth by X-ray or other forms of radiography. PEEK is radiolucent, while metal such as titanium blocks X-rays. In embodiments of the invention, in certain directions, there are provided certain line-of-sight views that are entirely through polymer with no presence of metal. For example, with PLIF implants 100, anatomically lateral views through some portion of the implant (or pair of implants) pass entirely through polymer. Similarly, for oblique implant 200, there are certain directions of view that pass entirely through polymer. For TLIF implants 300, anatomically Anterior-Posterior views through some portion of the implant pass entirely through polymer. With Lateral implant 400, anatomically Anterior-Posterior views through some portion of the implant 400 pass entirely through polymer. With Cervical implant 500, anatomically lateral views through some portion of the implant 500 pass entirely through polymer. In ALIF implant 600, at the midplane of the implant 600 (midway between the superior surface and the inferior surface), for much of the anatomically anterior-posterior dimension of implant 600, in an anatomically lateral view, there is a layer entirely of polymer and a view or line of sight that passes entirely through polymer.

It also can be seen that in most of the embodiments of the invention, the end component 120, 220, 320, 420, 520, 620 is metallic for reasons such as interface with installation instrument, while much of the rest of the implant is polymeric component 110, 210, 310, 410, 510A, 510B, 610. Therefore, for at least a majority of the bone-interfacing surface of the implant, the load path for compressive load in the vertical direction passes through polymeric material with the exception of end components 120, 220, 320, 420, 520A, 520B, 620 (and, in the case of the Cervical implant 500, an additional exception at the posterior of that implant). In general, including some polymer in the load path is desirable because the elastic modulus of the polymer is a better match to the modulus of bone than is the elastic modulus of titanium or similar metals. This helps to avoid the problem of stress-shielding.

FURTHER COMMENTS

Embodiments of the invention provide a combination of surfaces and materials that are osseointegrative, each in their own way. It is believed that the metal surfaces, which protrude slightly past the adjacent or nearby polymeric surfaces, will most influence the sliding and initial fit of the implant into the intervertebral space and the feel and tactile feedback to the surgeon upon guiding the implant into place. It is believed that this further provides surgeons with useful feel and tactile feedback during the surgical procedure. The porous metal of such surfaces also provides a favorable environment for bone to grow into. During surgery, the patient is generally in a horizontal position, with no axial compressive load on the spine due to body weight being exerted on or borne by the spine. After implantation, when weight (such as weight of some of the patient's body) is exerted on the implant and possibly there is some subsidence of the implant pressing into the vertebrae, there can be contact of bone with both the metal surface and also the polymeric surface on a particular bone-facing surface of the implant. In this situation, the geometric pattern of the polymeric component becomes active in load transfer and in resisting motion or expulsion of the implant. The metallic component, especially whatever surfaces of it are porous, can be conducive to osseointegration. The polymeric component can contain particles that are osteoconductive or otherwise improve the integration of the polymeric component with bone. Thus, each material or component can have its own role in osseointegration. In combination, the implant may have desirable elastic properties relative to the elastic properties of bone. In combination, the implant can have desirable radiological properties. However, it is not wished to be limited to any of this explanation.

Although the polymer has been disclosed as being polyetheretherketone (PEEK) or PEEK in combination with particles of an osseointegrative material, it would also be possible to use other polymers, as long as such other polymer has appropriate structural strength and biocompatibility, or other polymers in combination with an osseointegrative material. Although the osseointegrative material has been disclosed as being hydroxyapatite, it would also be possible to use other members of the calcium phosphate family, or other appropriate material. Specifically, it would be possible to use bioactive glass as the osseointegrative material. Any chemical or crystallographic form of calcium phosphate, or other osseointegrative materials, could also be used. The osseointegrative material could be osteoconductive or osteoinductive. Although the metal has been disclosed as being titanium or an alloy of titanium, it would also be possible to use other metals, as long as such other metal has appropriate structural strength and biocompatibility.

It is further possible that the polymeric component could contain an antimicrobial substance. One such possible substance is silver, silver compounds, or silver nanoparticles. Another possible substance is any of various antibiotics. Any such substance could be mixed together with the polymer during processing, or could be applied to it as a coating. Such substance could be applied to a metallic component or portion thereof as a coating.

The interior surface of the central opening 106, 206, 306, 406A, 406B, 506, 606 may have any or any combination of any or some or all of: a surface of polymeric material (which may contain particles of an osseointegrative material); a surface of a porous metal region; and a surface of a substantially solid metal region. It is believed that if porous metal is present at an edge of the central opening, the porous metal may help to encourage bone to "turn the corner" and grow from into the central opening. It is also possible that, if desired, some of the edge of the central opening may be substantially solid metal as may be desired for structural strength.

Although the metallic component has been disclosed as possibly having a porous region, it is also possible that the metallic component could instead be substantially solid metal having a surface that is roughened. Roughening could be accomplished by methods such as blasting with abrasive or grit, chemical etching, or other methods as known in the art. Porous regions are described as being made by additive manufacturing techniques such as three-dimensional printing. However, such porous regions could also be made by conventional sintering or by other techniques. Roughening processes could produce surfaces that have a root-mean-square roughness of less than 100 microns. The porous region may have a density less than 80% of the metal of which the metallic component is made. Substantially solid metallic regions may have a density that is more than 90% of the metal of which the metallic component is made. Still further, it is also possible that in a metallic component that has a porous region and a substantially solid region, the substantially solid region could be coated or treated by any of the described techniques.

In general, any combination of disclosed features, components and methods described herein is possible. Steps of a method can be performed in any order that is physically possible.

Although embodiments have been disclosed that are intervertebral spacers for spinal surgery, it is also possible for similar constructs to be used for other orthopedic implants and applications.

All cited references are incorporated by reference herein.

Although embodiments have been disclosed, it is not desired to be limited thereby. Rather, the scope should be determined only by the appended claims.

We claim:

1. An implantable device,
said device having a first bone-facing surface and an opposed second bone-facing surface and having a central opening extending from said first bone-facing surface to said second bone-facing surface,
said device comprising a polymeric component and a first metallic component on said first bone-facing surface and a second metallic component on said second bone-facing surface,
further comprising a pin, wherein said pin occupies a hole in said first metallic component and occupies a hole in said second metallic component and occupies a hole through said polymeric component,
wherein said pin is mechanically joined to said hole in said first metallic component and said pin is mechanically joined to said hole in said second metallic component,
wherein said first or said second metallic component comprises a porous region and a substantially solid region, said substantially solid region having a density at least 90% of a solid density of a metal of which said metallic component is made, said porous region having a density of less than 80% of a solid density of a metal of which said metallic component is made, and wherein said hole in said first metallic component or said second metallic component is entirely in said substantially solid region.

2. The device of claim 1, wherein said pin forms a first press-fit with said hole in said first metallic component and said pin forms a second press-fit with said hole in said second metallic component.

3. The device of claim 2, wherein a fit of said pin in said hole through said polymeric component is looser than a fit of said pin in either of said metallic components.

4. The device of claim 1, wherein said hole in said first metallic component is a through-hole and said hole in said second metallic component is a through-hole.

5. The device of claim 1, comprising a spot-weld between said pin and said one of said metallic components.

6. The device of claim 1, comprising a localized region of said pin or of one of said metallic components that is plastically deformed after assembly.

7. The device of claim 1, wherein one of said metallic components has a metallic component polymer-facing side surface and said polymeric component has a corresponding polymeric component metal-facing side surface, and wherein there is an interference fit between said metallic component polymer-facing side surface and said polymeric component metal-facing side surface.

8. An implantable device,
said device having a first bone-facing surface and an opposed second bone-facing surface and having a central opening extending from said first bone-facing surface to said second bone-facing surface,
said device comprising a polymeric component,
said device comprising a metallic component that is mechanically connected to said polymeric component, wherein said metallic component comprises a substantially solid region and a porous region, wherein said porous region of said metallic component has a density less than 80% of a density of metal of which said metallic component is made, and said substantially solid region has a density more than 90% of a density of metal of which said metallic component is made,
wherein said metallic component has a metallic component outwardly-facing surface that is part of one of said bone-facing surfaces, and said metallic component has a metallic component inwardly-facing surface opposed to said metallic component outwardly-facing surface,
wherein said metallic component inwardly-facing surface has at least a majority of its surface being said substantially solid region,
wherein said metallic component outwardly-facing surface contains both a surface of said porous region and a surface of said substantially solid region.

9. The device of claim 8, wherein said porous region integrally adjoins said substantially solid region on at least at least two interface surfaces that are generally perpendicular to each other.

10. The device of claim 8, wherein said substantially solid region underlies said porous region and said substantially solid region also contacts said porous region on a side surface of said porous region.

11. The device of claim 8, wherein said substantially solid region has a hole therethrough, wherein said device further comprises a pin, wherein said pin and said hole form a press-fit with each other.

12. The device of claim 8, wherein said device has a bone-facing surface that comprises said polymeric component and a surface of said porous region and a surface of said substantially solid region.

13. The device of claim 8, wherein said substantially solid region comprises a protrusion or cantilever that is continuous with both said porous region and another portion of said substantially solid region.

* * * * *